US005846946A

United States Patent [19]

Huebner et al.

[11] Patent Number: 5,846,946

[45] Date of Patent: Dec. 8, 1998

[54] COMPOSITIONS AND METHODS FOR ADMINISTERING BORRELIA DNA

[75] Inventors: Robert C. Huebner, Stroudsburg, Pa.; Jon A. Norman, Poway; Xiaowu Liang, La Jolla, both of Calif.; Kristin R. Carner, San Diego, Calif.; Alan G. Barbour; Catherine J. Luke, both of San Antonio, Tex.

[73] Assignees: Pasteur Merieux Serums et Vaccins, Lyon, France; Vical Inc., San Diego, Calif.; University of Texas Health Science Center, San Antonio, Tex.

[21] Appl. No.: 663,998

[22] Filed: Jun. 14, 1996

[51] Int. Cl.[6] .......... A61K 48/00

[52] U.S. Cl. .......... 514/44; 424/234.1; 435/6; 435/69.1; 435/172.3; 435/325; 435/320.1; 935/62; 935/56; 935/34; 935/65

[58] Field of Search .......... 424/234.1; 435/6, 435/69.1, 172.3, 325, 320.1; 514/44; 935/62, 56, 34, 65

[56] References Cited

U.S. PATENT DOCUMENTS

| | | | |
|---|---|---|---|
| 5,122,458 | 6/1992 | Post et al. | 435/69.1 |
| 5,558,993 | 9/1996 | Champion et al. | 435/6 |
| 5,571,718 | 11/1996 | Dunn et al. | 435/252.3 |
| 5,688,512 | 11/1997 | Bergstrom et al. | 424/234.1 |

FOREIGN PATENT DOCUMENTS

0346316 A2 12/1989 European Pat. Off. .

OTHER PUBLICATIONS

Robinson et al., Seminars in Immunology, vol. 9, pp. 271–283, 1997.

Barbour, Lyme Disease, the cause, the cure, the controversy. The Johns Hopkins University Press, 1997, pp. 240 and 241.

Probert et al. Infection and Immunity. May 1994. vol. 62(5):1920–6, May 9, 1998.

Bockenstedt et al. J. Innumology. 1993, 151(2):900–906, May 9, 1998.

Schaible et al. Vaccine. 1993, vol. 11(10):1049–54, May 9, 1998.

Montgomery et al. J. of Exp. Med. 1996, 183, 1:261–69.

Fikrig et al. Infection and Immunity. Feb. 1992. vol. 60, No. 2:657–661.

Rappuoli et al. Vaccine. 1996, vol. 14, No. 7:691–716.

Eisenbraun et al. DNA and Cell Biology. 1996, vol. 2, No. 3:168–175.

Mendoza–Vega et al. Applied Microb. Biotech. 1996 Jan. vol. 44(5):624–8.

Katsumi et al. Hum. Gene. Ther. 1994, 5:1335–1339.

Pardoll et al. Immunity. 1995, 3(2):165–9.

Robert Whalen. Emerging Infectious Diseases. 1996, vol. 2, No. 3:168–175.

*Primary Examiner*—Christopher S. F. Low
*Assistant Examiner*—Dave Trong Nguyen
*Attorney, Agent, or Firm*—Frommer Lawrence & Haug LLP; William S. Frommer; Thomas J. Kowalski

[57] ABSTRACT

Plasmid DNA encoding at least one Borrelia genospecies antigen and methods for making and using such a plasmid are disclosed and claimed. The genospecies can be burgdorferi, garinii and/or afzelli. The antigen can be OspA and/or OspB and/or OspC. Compositions containing the plasmid DNA are useful for administration to a host susceptible to Lyme Disease for an in vivo response, such as a protective response, or for generating useful antibodies. The inventive plasmid can also be transfected into cells for generating antigens in vitro. And, the inventive plasmid can be prepared by isolating DNA (such as DNA coding for: promoter, leader sequence, antigen, and terminator) and performing a ligation or ligations, such as a three-way ligation. More particularly, administration of DNA encoding Borrelia genospecies antigen, e.g., OspA and/or OspB and/or OspC and compositions therefor for eliciting an immunological response against Borrelia, such as a protective response preventive of Lyme Disease, are disclosed and claimed. Thus, Lyme Disease vaccines or immunological compositions, and methods of making and using them, are disclosed and claimed.

18 Claims, 37 Drawing Sheets

*FIG. 2A*

GTCACCGTCGTCGACCAGAGCTGAGATCCTACAGGAGTCCAGGGCTGGAGAGAAAACCTCTGC
GAGGAAAGGGAAGGAGCAAGCCGTGAATTTAAGGGACGCTGTGAAGCAATCATGGATGCAAT
GAAGAGAGGGCTCTGCTGTGTGCTGCTGCTGTGTGGAGCAGTCTTCGTTTCGCCCAGCGGTAC
FWD CTGTAAGCAAAATGTTAGCAGCCTTGACGAGAAAAACAGCGTTTCAGTAGATTTGCCTGGTGA
AATGAAAGTTCTTGTAAGCAAAGAAAAAAACAAAGACGGCAAGTACGATCTAATTGCAACAG
TAGACAAGCTTGAGCTTAAAGGAACTTCTGATAAAAACAATGGATCTGGAGTACTTGAAGGCG
TAAAAGCTGACAAAAGTAAAGTAAAATTAACAATTTCTGACGATCTAGGTCAAACCACACTTG
AAGTTTTCAAAGAAGATGGCAAAACACTAGTATCAAAAAAAGTAACTTCCAAAGACAAGTCA
TCAACAGAAGAAAAATTCAATGAAAAAGGTGAAGTATCTGAAAAAATAATAACAAGAGCAGA
CGGAACCAGACTTGAATACACAGAAATTAAAAGCGATGGATCTGGAAAAGCTAAAGAGGTTT
TAAAAGGCTATGTTCTTGAAGGAACTCTAACTGCTGAAAAAACAACATTGGTGGTTAAAGAAG
GAACTGTTACTTTAAGCAAAAATATTTCAAAATCTGGGGAAGTTTCAGTTGAACTTAATGACA
CTGACAGTAGTGCTGCTACTAAAAAAACTGCAGCTTGGAATTCAGGCACTTCAACTTTAACAA
TTACTGTAAACAGTAAAAAAACTAAAGACCTTGTGTTTACAAAAGAAAACACAATTACAGTAC
AACAATACGACTCAAATGGCACCAAATTAGAGGGGTCAGCAGTTGAAATTACAAAACTTGAT
REV GAAATTAAAAACGCTCTTAAGTAAGGAGAATTTTCTAGACCAGGCGCCTGGATCCAGATCTGC
TGTGCCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAGGTG
TCATTCTATTCTGGGGGGTGGGGTGGGGCAGCACAGCAAGGGGGAGGATTGGGAAGACAATA
GCAGGCATGCTGGGGATGCGGTGGGCTCTATGGGTACCCAGGTGCTGAAGAATTGACCCGGTT
CCTCCTGGGCCAGAAAGAAGCAGGCACATCCCCTTCTCTGTGACACACCCTGTCCACGCCCCT
GGTTCTTAGTTCCAGCCCCACTCATAGGACACTCATAGCTCAGGAGGGCTCCGCCTTCAATCCC
ACCCGCTAAAGTACTTGGAGCGGTCTCTCCCTCCCTCATCAGCCCACCAAACCAAACCTAGCCT

FIG. 2B

CCAAGAGTGGGAAGAAATTAAAGCAAGATAGGCTATTAAGTGCAGAGGGAGAGAAAATGCCT
CCAACATGTGAGGAAGTAATGAGAGAAATCATAGAATTTCTTCCGCTTCCTCGCTCACTGACT
CGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCA
TCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCAATGCTCACGCTGTAGGTATCTCAGT
TCGGTGTAGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCACTGGC
AGCAGCCACTGGTAACAGGATTAGCAGAGCGAGGTATGTAGGCGGTGCTACAGAGTTCTTGA
AGTGGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTT
TGATCTTTTCTACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCGGGGGGGGGGGCGCTGAG
GTCTGCCTCGTGAAGAAGGTGTTGCTGACTCATACCAGGCCTGAATCGCCCCATCATCCAGCC
AGAAAGTGAGGGAGCCACGGTTGATGAGAGCTTTGTTGTAGGTGGACCAGTTGGTGATTTTGA
ACTTTTGCTTTGCCACGGAACGGTCTGCGTTGTCGGGAAGATGCGTGATCTGATCCTTCAACTC
AGCAAAAGTTCGATTTATTCAACAAAGCCGCCGTCCCGTCAAGTCAGCGTAATGCTCTGCCAG
TGTTACAACCAATTAACCAATTCTGATTAGAAAAACTCATCGAGCATCAAATGAAACTGCAAT

FIG.2C

TTATTCATATCAGGATTATCAATACCATATTTTTGAAAAAGCCGTTTCTGTAATGAAGGAGAA
AACTCACCGAGGCAGTTCCATAGGATGGCAAGATCCTGGTATCGGTCTGCGATTCCGACTCGT
CCAACATCAATACAACCTATTAATTTCCCCTCGTCAAAAATAAGGTTATCAAGTGAGAAATCA
CCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTC
GTGATTGCGCCTGAGCGAGACGAAATACGCGATCGCTGTTAAAAGGACAATTACAAACAGGA
ATCGAATGCAACCGGCGCAGGAACACTGCCAGCGCATCAACAATATTTTCACCTGAATCAGGA
TATTCTTCTAATACCTGGAATGCTGTTTTCCCGGGGATCGCAGTGGTGAGTAACCATGCATCAT
CAGGAGTACGGATAAAATGCTTGATGGTCGGAAGAGGCATAAATTCCGTCAGCCAGTTTAGTC
TGACCATCTCATCTGTAACATCATTGGCAACGCTACCTTTGCCATGTTTCAGAAACAACTCTGG
CGCATCGGGCTTCCCATACAATCGATAGATTGTCGCACCTGATTGCCCGACATTATCGCGAGCC
CATTTATACCCATATAAATCAGCATCCATGTTGGAATTTAATCGCGGCCTCGAGCAAGACGTTT
CCCGTTGAATATGGCTCATAACACCCCTTGTATTACTGTTTATGTAAGCAGACAGTTTTATTGT
TCATGATGATATATTTTTATCTTGTGCAATGTAACATCAGAGATTTTGAGACACAACGTGGCTT
TCCCCCCCCCCCCATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCT
TTCGTCTCGCGCGTTTCGGTGATGACGGTGAAAACCTCTGACACATGCAGCTCCCGGAGACGG
TCACAGCTTGTCTGTAAGCGGATGCCGGGAGCAGACAAGCCCGTCAGGGCGCGTCAGCGGGT
GTTGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGATTGGCTATT
GGCCATTGCATACGTTGTATCCATATCATAATATGTACATTTATATTGGCTCATGTCCAACATT
ACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCG

FIG. 2D

CCCAACGACCCCCGCCCATTGACGTCAATAATGACGTATGTTCCCATAGTAACGCCAATAGGG
ACTTTCCATTGACGTCAATGGGTGGAGTATTTACGGTAAACTGCCCACTTGGCAGTACATCAA
GTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCG
CTATTACCATGGTGATGCGGTTTTGGCAGTACATCAATGGGCGTGGATAGCGGTTTGACTCAC
GGGGATTTCCAAGTCTCCACCCCATTGACGTCAATGGGAGTTTGTTTTGGCACCAAAATCAAC
GGGACTTTCCAAAATGTCGTAACAACTCCGCCCCATTGACGCAAATGGGCGGTAGGCGTGTAC
GGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCGGGAACGGT
GCATTGGAACGCGGATTCCCCGTGCCAAGAGTGACGTAAGTACCGCCTATAGAGTCTATAGGC
CCACCCCCTTGGCTTCTTATGCATGCTATACTGTTTTTGGCTTGGGGTCTATACACCCCCGCTTC
CTCATGTTATAGGTGATGGTATAGCTTAGCCTATAGGTGTGGGTTATTGACCATTATTGACCAC
TCCCCTATTGGTGACGATACTTTCCATTACTAATCCATAACATGGCTCTTTGCCACAACTCTCTT
TATTGGCTATATGCCAATACACTGTCCTTCAGAGACTGACACGGACTCTGTATTTTTACAGGAT
GGGGTCTCATTTATTATTTACAAATTCACATATACAACACCACCGTCCCCAGTGCCCGCAGTTT
TTATTAAACATAACGTGGGATCTCCACGCGAATCTCGGGTACGTGTTCCGGACATGGGCTCTTC
TCCGGTAGCGGCGGAGCTTCTACATCCGAGCCCTGCTCCCATGCCTCCAGCGACTCATGGTCGC
TCGGCAGCTCCTTGCTCCTAACAGTGGAGGCCAGACTTAGGCACAGCACGATGCCCACCACCA
CCAGTGTGCCGCACAAGGCCGTGGCGGTAGGGTATGTGTCTGAAAATGAGCTCGGGGAGCGG
GCTTGCACCGCTGACGCATTTGGAAGACTTAAGGCAGCGGCAGAAGAAGATGCAGGCAGCTG
AGTTGTTGTGTTCTGATAAGAGTCAGAGGTAACTCCCGTTGCGGTGCTGTTAACGGTGGAGGG
CAGTGTAGTCTGAGCAGTACTCGTTGCTGCCGCGCGCGCCACCAGACATAATAGCTGACAGAC
TAACAGACTGTTCCTTTCCATGGGTCTTTTCTGCA

FIG.4A

```
FWD CTGTGCACAAAAAGGTGCTGAGTCAATTGGTTCTCAAAAAGAAAATGATCTAAACCTTGAAGA
    CTCTAGTAAAAAATCACATCAAAACGCTAAACAAGACCTTCCTGCGGTGACAGAAGACTCAGT
    GTCTTTGTTTAATGGTAATAAAATTTTTGTAAGCAAAGAAAAAAATAGCTCCGGCAAATATGA
    TTTAAGAGCAACAATTGATCAGGTTGAACTTAAAGGAACTTCCGATAAAAACAATGGTTCTGG
    AACCCTTGAAGGTTCAAAGCCTGACAAGAGTAAAGTAAAATTAACAGTTTCTGCTGATTTAAA
    CACAGTAACCTTAGAAGCATTTGATGCCAGCAACCAAAAAATTTCAAGTAAAGTTACTAAAAA
    ACAGGGGTCAATAACAGAGGAAACTCTCAAAGCTAATAAATTAGACTCAAAGAAATTAACAA
    GATCAAACGGAACTACACTTGAATACTCACAAATAACAGATGCTGACAATGCTACAAAAGCA
    GTAGAAACTCTAAAAAATAGCATTAAGCTTGAAGGAAGTCTTGTAGTCGGAAAAACAACAGT
    GGAAATTAAAGAAGGTACTGTTACTCTAAAAAGAGAAATTGAAAAAGATGGAAAAGTAAAAG
    TCTTTTTGAATGACACTGCAGGTTCTAACAAAAAAACAGGTAAATGGAAGACAGTACTAGCA
    CTTTAACAATTAGTGCTGACAGCAAAAAAACTAAAGATTTGGTGTTCTTAACAGATGGTACAA
    TTACAGTACAACAATACAACACAGCTGGAACCAGCCTAGAAGGATCAGCAAGTGAAATTAAA
REV AATCTTTCAGAGCTTAAAAACGCTTTAAAATAATATATAGGATCCAGATCTGCTGTGCCTTCTA
    GTTGCCAGCCATCTGTTGTTTGCCCCTCCCCCGTGCCTTCCTTGACCCTGGAAGGTGCCACTCC
    CACTGTCCTTTCCTAATAAAATGAGGAAATTGCATCGCATTGTCTGAGTAGGTGTCATTCTATT
    CTGGGGGGTGGGGTGGGGCAGCACAGCAAGGGGGAGGATTGGGAAGACAATAGCAGGCATG
    CTGGGGATGCGGTGGGCTCTATGGGTACCCAGGTGCTGAAGAATTGACCCGGTTCCTCCTGGG
    CCAGAAAGAAGCAGGCACATCCCCTTCTCTGTGACACACCCTGTCCACGCCCCTGGTTCTTAGT
    TCCAGCCCCACTCATAGGACACTCATAGCTCAGGAGGGCTCCGCCTTCAATCCCACCCGCTAA
    AGTACTTGGAGCGGTCTCTCCCTCCCTCATCAGCCCACCAAACCAAACCTAGCCTCCAAGAGT
    GGGAAGAAATTAAAGCAAGATAGGCTATTAAGTGCAGAGGGAGAGAAAATGCCTCCAACATG
    TGAGGAAGTAATGAGAGAAATCATAGAATTTCTTCCGCTTCCTCGCTCACTGACTCGCTGCGCT
    CGGTCGTTCGGCTGCGGCGAGCGGTATCAGCTCACTCAAAGGCGGTAATACGGTTATCCACAG
```

FIG. 4B

AATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGCCTTT
CTCCCTTCGGGAAGCGTGGCGCTTTCTCAATGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATC
CGGTAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTTTTTT
GTTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCT
GTCTATTTCGTTCATCCATAGTTGCCTGACTCCGGGGGGGGGGGGCGCTGAGGTCTGCCTCGTG
AAGAAGGTGTTGCTGACTCATACCAGGCCTGAATCGCCCCATCATCCAGCCAGAAAGTGAGGG
AGCCACGGTTGATGAGAGCTTTGTTGTAGGTGGACCAGTTGGTGATTTTGAACTTTTGCTTTGC
CACGGAACGGTCTGCGTTGTCGGGAAGATGCGTGATCTGATCCTTCAACTCAGCAAAAGTTCG
ATTTATTCAACAAAGCCGCCGTCCCGTCAAGTCAGCGTAATGCTCTGCCAGTGTTACAACCAA
TTAACCAATTCTGATTAGAAAAACTCATCGAGCATCAAATGAAACTGCAATTTATTCATATCA
GGATTATCAATACCATATTTTTGAAAAAGCCGTTTCTGTAATGAAGGAGAAAACTCACCGAGG
CAGTTCCATAGGATGGCAAGATCCTGGTATCGGTCTGCGATTCCGACTCGTCCAACATCAATA
CAACCTATTAATTTCCCCTCGTCAAAAATAAGGTTATCAAGTGAGAAATCACCATGAGTGACG
ACTGAATCCGGTGAGAATGGCAAAAGCTTATGCATTTCTTTCCAGACTTGTTCAACAGGCCAG

FIG. 4C

CCATTACGCTCGTCATCAAAATCACTCGCATCAACCAAACCGTTATTCATTCGTGATTGCGCCT
GAGCGAGACGAAATACGCGATCGCTGTTAAAAGGACAATTACAAACAGGAATCGAATGCAAC
CGGCGCAGGAACACTGCCAGCGCATCAACAATATTTTCACCTGAATCAGGATATTCTTCTAAT
ACCTGGAATGCTGTTTTCCCGGGGATCGCAGTGGTGAGTAACCATGCATCATCAGGAGTACGG
ATAAAATGCTTGATGGTCGGAAGAGGCATAAATTCCGTCAGCCAGTTTAGTCTGACCATCTCA
TCTGTAACATCATTGGCAACGCTACCTTTGCCATGTTTCAGAAACAACTCTGGCGCATCGGGCT
TCCCATACAATCGATAGATTGTCGCACCTGATTGCCCGACATTATCGCGAGCCCATTTATACCC
ATATAAATCAGCATCCATGTTGGAATTTAATCGCGGCCTCGAGCAAGACGTTTCCCGTTGAAT
ATGGCTCATAACACCCCTTGTATTACTGTTTATGTAAGCAGACAGTTTTATTGTTCATGATGAT
ATATTTTTATCTTGTGCAATGTAACATCAGAGATTTTGAGACACAACGTGGCTTTCCCCCCCCC
CCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAG
AAACCATTATTATCATGACATTAACCTATAAAAATAGGCGTATCACGAGGCCCTTTCGTCTCGC
GCGTTTCGGTGATGACGGTGAAAACCTCTGACACATGCAGCTCCCGGAGACGGTCACAGCTTG
TCTGTAAGCGGATGCCGGGAGCAGACAAGCCCGTCAGGGCGCGTCAGCGGGTGTTGGCGGGT
GTCGGGGCTGGCTTAACTATGCGGCATCAGAGCAGATTGTACTGAGAGTGCACCATATGCGGT
GTGAAATACCGCACAGATGCGTAAGGAGAAAATACCGCATCAGATTGGCTATTGGCCATTGCA
TACGTTGTATCCATATCATAATATGTACATTTATATTGGCTCATGTCCAACATTACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTTTCCATTG

ACGTCAATGGGTGGAGTATTTACGGTAAACTGCCCACTTGGCAGTACATCAAGTGTATCATAT
GCCAAGTACGCCCCCTATTGACGTCAATGACGGTAAATGGCCCGCCTGGCATTATGCCCAGTA
CATGACCTTATGGGACTTTCCTACTTGGCAGTACATCTACGTATTAGTCATCGCTATTACCATG
GTGATGCGGTTTTGGCAGTACATCAATGGGCGTGGATAGCGGTTTGACTCACGGGGATTTCCA
AGTCTCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTGGGAGGTC
TATATAAGCAGAGCTCGTTTAGTGAACCGTCAGATCGCCTGGAGACGCCATCCACGCTGTTTT
GACCTCCATAGAAGACACCGGGACCGATCCAGCCTCCGCGGCCGGGAACGGTGCATTGGAAC
GCGGATTCCCCGTGCCAAGAGTGACGTAAGTACCGCCTATAGAGTCTATAGGCCCACCCCCTT
GGCTTCTTATGCATGCTATACTGTTTTTGGCTTGGGGTCTATACACCCCCGCTTCCTCATGTTAT
AGGTGATGGTATAGCTTAGCCTATAGGTGTGGGTTATTGACCATTATTGACCACTCCCCTATTG
GTGACGATACTTTCCATTACTAATCCATAACATGGCTCTTTGCCACAACTCTCTTTATTGGCTAT
ATGCCAATACACTGTCCTTCAGAGACTGACACGGACTCTGTATTTTTACAGGATGGGGTCTCAT
TTATTATTTACAAATTCACATATACAACACCACCGTCCCCAGTGCCCGCAGTTTTTATTAAACA
TAACGTGGGATCTCCACGCGAATCTCGGGTACGTGTTCCGGACATGGGCTCTTCTCCGGTAGC
GGCGGAGCTTCTACATCCGAGCCCTGCTCCCATGCCTCCAGCGACTCATGGTCGCTCGGCAGCT
CCTTGCTCCTAACAGTGGAGGCCAGACTTAGGCACAGCACGATGCCCACCACCACCAGTGTGC
CGCACAAGGCCGTGGCGGTAGGGTATGTGTCTGAAAATGAGCTCGGGGAGCGGGCTTGCACC
GCTGACGCATTTGGAAGACTTAAGGCAGCGGCAGAAGAAGATGCAGGCAGCTGAGTTGTTGT
GTTCTGATAAGAGTCAGAGGTAACTCCCGTTGCGGTGCTGTTAACGGTGGAGGGCAGTGTAGT
CTGAGCAGTACTCGTTGCTGCCGCGCGCCACCAGACATAATAGCTGACAGACTAACAGACT
GTTCCTTTCCATGGGTCTTTTCTGCAGTCACCGTCGTCGACCAGAGCTGAGATCCTACAGGAGT
CCAGGGCTGGAGAGAAAACCTCTGCGAGGAAAGGGAAGGAGCAAGCCGTGAATTTAAGGGA
CGCTGTGAAGCAATCATGGATGCAATGAAGAGAGGGCTCTGCTGTGTGCTGCTGCTGTGTGGA
GCAGTCTTCGTTTCGCCCAGCGGTAC

GATCCNNNNNNNNNNNNNNNNNNNNNNNNAAGCTTAATTAGAACCAAACTTAATTAAAACCA
AACTTAATTGAAGTTATTATCATTTTATTTTTTTTCAATTTTCTATTTGTTATTTGTTAATCTTAT
AATATAATTATACTTGTATTAAGTTATATTAATATAAAAGGAGAATATATTATGAAAAAATAT
TTATTGGGAATAGGTCTAATATTAGCCTTAATAGCATGTAAGCAAAATGTTAGCAGCCTTGAC
GAGAAAAACAGCGTTTCAGTAGATTTGCCTGGTGAAATGAAAGTTCTTGTAAGCAAAGAAAA
AAACAAAGACGGCAAGTACGATCTAATTGCAACAGTAGACAAGCTTGAGCTTAAAGGAACTT
CTGATAAAAACAATGGATCTGGAGTACTTGAAGGCGTAAAAGCTGACAAAAGTAAAGTAAAA
TTAACAATTTCTGACGATCTAGGTCAAACCACACTTGAAGTTTTCAAAGAAGATGGCAAAACA
CTAGTATCAAAAAAAGTAACTTCCAAAGACAAGTCATCAACAGAAGAAAAATTCAATGAAAA
AGGTGAAGTATCTGAAAAAATAATAACAAGAGCAGACGGAACCAGACTTGAATACACAGAAA
TTAAAAGCGATGGATCTGGAAAAGCTAAAGAGGTTTTAAAAGGCTATGTTCTTGAAGGAACTC
TAACTGCTGAAAAAACAACATTGGTGGTTAAAGAAGGAACTGTTACTTTAAGCAAAAATATTT
CAAAATCTGGGGAAGTTTCAGTTGAACTTAATGACACTGACAGTAGTGCTGCTACTAAAAAAA
CTGCAGCTTGGAATTCAGGCACTTCAACTTTAACAATTACTGTAAACAGTAAAAAAACTAAAG
ACCTTGTGTTTACAAAAGAAAACACAATTACAGTACAACAATACGACTCAAATGGCACCAAAT
TAGAGGGGTCAGCAGTTGAAATTACAAAACTTGATGAAATTAAAAACGCTTTAAAATAAGGA
GAATTTATGAGATTATTAATAGGATTTGCTTTAGCGTTAGCTTTAATAGGATGTGCACAAAAA
GGTGCTGAGTCNNNNNNNNGTTGGGAATTCGTAATCATGGTCATAGCTGTTTCCTGTGTGAAA
TTGTTATCCGCTCACAATTCCACACAACATACGAGCCGGAAGCATAAAGTGTAAAGCCTGGGG
TGCCTAATGAGTGAGCTAACTCACATTAATTGCGTTGCGCTCACTGCCCGCTTTCCAGTCGGGA
AACCTGTCGTGCCAGCTGCATTAATGAATCGGCCAACGCGCGGGGAGAGGCGGTTTGCGTATT
GGGCGCTCTTCCGCTTCCTCGCTCACTGACTCGCTGCGCTCGGTCGTTCGGCTGCGGCGAGCGG

FIG. 5B

TATCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGCG
AAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGA
CAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCC
GGAAGGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTC
TGAGAATAGTGTATGCGGCGACCGAGTTGCTCTTGCCCGGCGTCAATACGGGATAATACCGCG

FIG. 5C

CCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAA
AGGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAAC
AAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTCTCGCGCGTTTCGGTGA
TGACGGTGAAAACCTCTGACACATGCAGCTCCCGGAGACGGTCACAGCTTGTCTGTAAGCGGA
TGCCGGGAGCAGACAAGCCCGTCAGGGCGCGTCAGCGGGTGTTGGCGGGTGTCGGGGCTGGC
TTAACTATGCGGCATCAGAGCAGATTGTACTGAGAGTGCACCATATGCGGTGTGAAATACCGC
ACAGATGCGTAAGGAGAAAATACCGCATCAGGCGCCATTCGCCATTCAGGCTGCGCAACTGTT
GGGAAGGGCGATCGGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTTGTAAAACGACGGCC
AGTGCCAAGCTTGGCTGCAGGTCGACGCTCTCCCTTATGCGACTCCTGCATTAGGAAGCAGCC
CAGTAGTAGGTTGAGGCCGTTGAGCACCGCCGCCGCAAGGAATGGTGCATGCAAGGAGATGG
CGCCCAACAGTCCCCCGGCCACGGGGCCTGCCACCATACCCACGCCGAAACAAGCGCTCATGA
GCCCGAAGTGGCGAGCCCGATCTTCCCCATCGGTGATGTCGGCGATATAGGCGCCAGCAACCG
CACCTGTGGCGCCGGTGATGCCGGCCACGATGCGTCCGGCGTAGAG

FIG. 6A

AATTCAGGCACTTCAACTTTAACAATTACTGTAAACAGTAAAAAAACTAAAGACCTTGTGTTT
ACAAAAGAAAACACAATTACAGTACAACAATACGACTCAAATGGCACCAAATTAGAGGGGTC
AGCAGTTGAAATTACAAAACTTGATGAAATTAAAAACGCTTTAAAATAAGGAGAATTTATGA
GATTATTAATAGGATTTGCTTTAGCGTTAGCTTTAATAGGATGTGCACAAAAAGGTGCTGAGT
CAATTGGTTCTCAAAAAGAAAATGATCTAAACCTTGAAGACTCTAGTAAAAAATCACATCAAA
ACGCTAAACAAGACCTTCCTGCGGTGACAGAAGACTCAGTGTCTTTGTTTAATGGTAATAAAA
TTTTTGTAAGCAAAGAAAAAAATAGCTCCGGCAAATATGATTTAAGAGCAACAATTGATCAGG
TTGAACTTAAAGGAACTTCCGATAAAAACAATGGTTCTGGAACCCTTGAAGGTTCAAAGCCTG
ACAAGAGTAAAGTAAAATTAACAGTTTCTGCTGATTTAAACACAGTAACCTTAGAAGCATTTG
ATGCCAGCAACCAAAAAATTTCAAGTAAAGTTACTAAAAAACAGGGGTCAATAACAGAGGAA
ACTCTCAAAGCTAATAAATTAGACTCAAAGAAATTAACAAGATCAAACGGAACTACACTTGA
ATACTCACAAATAACAGATGCTGACAATGCTACAAAAGCAGTAGAAACTCTAAAAAATAGCA
TTAAGCTTGAAGGAAGTCTTGTAGTCGGAAAAACAACAGTGGAAATTAAAGAAGGTACTGTT
ACTCTAAAAAGAGAAATTGAAAAAGATGGAAAAGTAAAAGTCTTTTTGAATGACACTGCAGG
TTCTAACAAAAAAACAGGTAAATGGGAAGACAGTACTAGCACTTTAACAATTAGTGCTGACA
GCAAAAAAACTAAAGATTTGGTGTTCTTAACAGATGGTACAATTACAGTACAACAATACAACA
CAGCTGGAACCAGCCTAGAAGGATCAGCAAGTGAAATTAAAAATCTTTCAGAGCTTAAAAAC
GCTTTAAAATAATATATAAGTAAACCCCCTACAAGGCATCAGCTAGTGTAGGAAGNNNNNNN
NGGCCNNNNNNNNGTTGGGGATCCGTCGACCTGCAGCCAAGCTTGGCGTAATCATGGTCATA
GCTGTTTCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCGCTCGGTC

FIG. 6B

GTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCTTTTCTAC
GGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGT
CTATTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGA

FIG. 6C

GTACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTCG
TGCACCCAACTGATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATACATATTTGAA
TGTATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCCTTT
CGTCTCGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCACCA
TATGCGGTGTGAAATACCGCACAGATGCGTAAGGAGAAAATACCGCATCAGGCGCCATTCGC
CATTCAGGCTGCGCAACTGTTGGGAAGGGCGATCGGTGCGGGCCTCTTCGCTATTACGCCAGC
TGGCGAAAGGGGGATGTGCTGCAAGGCGATTAAGTTGGGTAACGCCAGGGTTTTCCCAGTCAC
GACGTTGTAAAACGACGGCCAGTG

CTACCTTAATTAGAACCAAACTTAATTAAAACCAAACTTAATTGAAGTTATTATCATTTTA
60

10
TTTTTTTTTCAATTTTTCTATTTGTTATTTTGTTAATCTTATAATATAATTATACTTGTATTA
P2 P1 P2 120
Kpn I

OspA ->
1 10
MetLysLysTyrLeuLeuGlyIleGlyLeu
AGTTATATTAATATAAAACGAGAATATATTATGAAAAAATATTTATTCGGAATACGTCTA
RBS 180

20 30
IleLeuAlaLeuIleAlaCysLysGlnAsnValSerSerLeuAspGluLysAsnSerVal
ATATTACCCTTAATAGCATGTAACCAAAATGTTACCAGCCTTGACGAGAAAAACACCGTT
240

FIG. 7A 40 50
SerValAspLeuProGlyGluMetLysValLeuValSerLysGluLysAsnLysAspGly
TCAGTAGATTTGCCTGGTGAAATGAAAGTTCTTGTAAGCAAAGAAAAAAACAAAGACGGC
300

60 70
LysTyrAspLeuIleAlaThrValAspLysLeuGluLeuLysGlyThrSerAspLysAsn
AAGTACGATCTAATTGCAACAGTAGACAAGCTTGAGCTTAAAGGAACTTCTGATAAAAAC
360

80 90
AsnGlySerGlyValLeuGluGlyValLysAlaAspLysSerLysValLysLeuThrIle
AATGGATCTGGAGTACTTGAAGGCGTAAAAGCTGACAAAAGTAAAGTAAAATTAACAATT
420

100 110
SerAspAspLeuGlyGlnThrThrLeuGluValPheLysGluAspGlyLysThrLeuVal
TCTGACGATCTAGGTCAAACCACACTTGAAGTTTTCAAAGAAGATGGCAAAACACTAGTA
480

FIG. 7B 120 130
SerLysLysValThrSerLysAspLysSerSerThrGluGluLysPheAsnGluLysGly
TCAAAAAAAGTAACTTCCAAAGACAAGTCATCAACAGAAGAAAAATTCAATGAAAAAGGT
540

140 150
GluValSerGluLysIleIleThrArgAlaAspGlyThrArgLeuGluTyrThrGlyIle
GAAGTATCTGAAAAAATAATAACAAGAGCAGACGGAACCAGACTTGAATACACAGGAATT
600

160 170
LysSerAspGlySerGlyLysAlaLysGluValLeuLysGlyTyrValLeuGluGlyThr
AAAAGCGATGGATCTGGAAAAGCTAAAGAGGTTTTAAAAGGCTATGTTCTTGAAGGAACT
660

180 190
LeuThrAlaGluLysThrThrLeuValValLysGluGlyThrValThrLeuSerLysAsn
CTAACTGCTGAAAAAACAACATTGGTGGTTAAAGAAGGAACTGTTACTTTAAGCAAAAAT
720

FIG. 7C 200 210
IleSerLysSerGlyGluValSerValGluLeuAsnAspThrAspSerSerAlaAlaThr
ATTTCAAAATCTGGGGAAGTTTCAGTTGAACTTAATGACACTGACAGTAGTCCTGCTACT
780

220 230
LysLysThrAlaAlaTrpAsnSerGlyThrSerThrLeuThrIleThrValAsnSerLys
AAAAAAACTGCAGCTTGGAATTCAGGCACTTCAACTTTAACAATTACTGTAAACAGTAAA
840

240 250
LysThrLysAspLeuValPheThrLysGluAsnThrIleThrValGlnGlnTyrAspSer
AAAACTAAAGACCTTGTGTTTACAAAAGAAAACACAATTACAGTACAACAATACGACTCA
900

260 270
AsnGlyThrLysLeuGluGlySerAlaValGluIleThrLysLeuAspGluIleLysAsn
AATGGCACCAAATTAGAGGGGTCAGCAGTTGAAATTACAAAACTTGATGAAATTAAAAAC
960

Kpn I →

FIG. 7D

```
                     OspB------>
                     1                                       10
AlaLeuLys***         MetArgLeuLeuIleGlyPheAlaLeuAlaLeuAlaLeu
GCTTTAAAATAACGAGAATTTATGAGATTATTAATAGGATTTGCTTTAGCGTTACCTTTA
                                                          1020
<------------- RBS ----------
               Xba I

                   20                                      30
IleGlyCysAlaGlnLysGlyAlaGluSerIleGlySerGlnLysGluAsnAspLeuAsn
ATAGGATGTGCACAAAAAGGTGCTGAGTCAATTGGTTCTCAAAAAGAAAATGATCTAAAC
                                                          1080

                   40                                      50
LeuGluAspSerSerLysLysSerHisGlnAsnAlaLysGlnAspLeuProAlaValThr
CTTGAAGACTCTAGTAAAAAATCACATCAAAACGCTAAACAAGACCTTCCTGCGGTGACA
                                                          1140

                   60                                      70
GluAspSerValSerLeuPheAsnGlyAsnLysIlePheValSerLysGluLysAsnSer
GAAGACTCAGTGTCTTTGTTTAATGGTAATAAAATTTTTGTAAGCAAAGAAAAAAATAGC
                                                          1200
```

FIG. 7E

```
        80                                      90
SerGlyLysTyrAspLeuArgAlaThrIleAspGlnValGluLeuLysGlyThrSerAsp
TCCGGCAAATATGATTTAAGAGCAACAATTGATCAGGTTGAACTTAAAGGAACTTCCGAT
                                                        1260

        100                                     110
LysAsnAsnGlySerGlyThrLeuGluGlySerLysProAspLysSerLysValLysLeu
AAAAACAATGGTTCTGGAACCCTTGAAGGTTCAAAGCCTGACAAGAGTAAAGTAAAATTA
                                                        1320

        120                                     130
ThrValSerAlaAspLeuAsnThrValThrLeuGluAlaPheAspAlaSerAsnGlnLys
ACAGTTTCTGCTGATTTAAACACAGTAACCTTAGAAGCATTTGATGCCAGCAACCAAAAA
                                                        1380

        140                                     150
IleSerSerLysValThrLysLysGlnGlySerIleThrGluGluThrLeuLysAlaAsn
ATTTCAAGTAAAGTTACTAAAAAACAGGGGTCAATAACAGAGGAAACTCTCAAAGCTAAT
                                                        1440
```

FIG. 7F 160 170
LysLeuAspSerLysLysLeuThrArgSerAsnGlyThrThrLeuGluTyrSerGlnIle
AAATTAGACTCAAAGAAATTAACAAGATCAAACGGAACTACACTTGAATACTCACAAATA
1500

180 190
ThrAspAlaAspAsnAlaThrLysAlaValGluThrLeuLysAsnSerIleLysLeuGlu
ACAGATGCTGACAATGCTACAAAAGCAGTAGAAACTCTAAAAAATAGCATTAAGCTTGAA
1560

200 210
GlySerLeuValValGlyLysThrThrValGluIleLysGluGlyThrValThrLeuLys
GGAAGTCTTGTAGTCGGAAAAACAACAGTGGAAATTAAAGAAGGTACTGTTACTCTAAAA
1620

220 230
ArgGluIleGluLysAspGlyLysValLysValPheLeuAsnAspThrAlaGlySerAsn
AGAGAAATTGAAAAAGATGGAAAAGTAAAAGTCTTTTTGAATGACACTGCAGGTTCTAAC
:680

FIG. 7G 240 250
LysLysThrGlyLysTrpGluAspSerThrSerThrLeuThrIleSerAlaAspSerLys
AAAAAAACAGGTAAATGGGAAGACAGTACTAGCACTTTAACAATTAGTGCTGACAGCAAA
1740

260 270
LysThrLysAspLeuValPheLeuThrAspGlyThrIleThrValGlnGlnTyrAsnThr
AAAACTAAAGATTTGGTGTTCTTAACAGATGGTACAATTACAGTACAACAATACAACACA
1800

280 290
AlaGlyThrSerLeuGluGlySerAlaSerGluIleLysAsnLeuSerGluLeuLysAsn
GCTGGAACCAGCCTAGAAGGATCAGCAAGTGAAATTAAAAATCTTTCAGAGCTTAAAAAC
1860

AlaLeuLys***
GCTTTAAAATAATATATAAGTAAACCCCCTACAAGGCATCAGCTAGTGTAGGAAG

BamH1

3' IE Acceptor Site

Pst ▼ SalI

1841 GTTCCTTTCCATGGGTCTTTTCTGCAGTCACCGTCGTCGA
CAAGGAAAGGTACCCAGAAAAGACGTCAGTGGCAGCAGCT

PmlI BclI EcoRV NotI XbaI BstHI HarI

1881 CACGTGTGATCAGATATCGCGGCCGCTCTAGACCAGGCGC
GTGCACACTAGTCTATAGCGCCGGCGAGATCTGGTCCGCG

1921 CTGGATCCAGATCTGCTGTGCCTTCTAGTTGCCAGCCATC
GACCTAGGTCTAGACGACACGGAAGATCAACGGTCGGTAG

1961 TGTTGTTTGCCCCTCCCCCGTGCCTTCCTTGACCCTGGAA
ACAACAAACGGGGAGGGGGCACGGAAGGAACTGGGACCTT

2001 G BamHI Bgl2

VR1012 Sequence

CTCGCGCGTTTCGGTGATGACGGTGAAAACCTCTGACACATGCAGCTCCCGGA
GACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGA
TGCGTAAGGAGAAAATACCGCATCAGATTGGCTATTGGCCATTGCATACGTTGT
ATCCATATCATAATATGTACATTTATATTGGCTCATGTCCAACATTACCGCCATG
TTGACATTGATTATTGACTAGTTATTAATAGTAATCAATTACGGGGTCATTAGTT
CATAGCCCATATATGGAGTTCCGCGTTACATAACTTACGGTAAATGGCCCGCCT
GGCTGACCGCCCAACGACCCCCGCCCATTGACGTCAATAATGACGTATGTTCC
CATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCC
TATTGACGTCAATGACGGTAAATGGCCCGCCTGGCATTATGCCCAGTACATGAC
CTTATGGGACTTTCCTACTTGGCAGTACATCTACGTATTAGTCATCGCTATTACC
ATGGTGATGCGGTTTTGGCAGTACATCAATGGGCGTGGATAGCGGTTTGACTC
ACGGGGATTTCCAAGTCTCCACCCCATTGACGTCAATGGGAGTTTGTTTTGGCA
CCAAAATCAACGGGACTTTCCAAAATGTCGTAACAACTCCGCCCCATTGACGCA
AATGGGCGGTAGGCGTGTACGGTGGGAGGTCTATATAAGCAGAGCTCGTTTAG
TGAACCGTCAGATCGCCTGGAGACGCCATCCACGCTGTTTTGACCTCCATAGAA
GACACCGGGACCGATCCAGCCTCCGCGGCCGGGAACGGTGCATTGGAACGCG
GATTCCCCGTGCCAAGAGTGACGTAAGTACCGCCTATAGAGTCTATAGGCCCA
CCCCCTTGGCTTCTTATGCATGCTATACTGTTTTTGGCTTGGGGTCTATACACCC
CCGCTTCCTCATGTTATAGGTGATGGTATAGCTTAGCCTATAGGTGTGGGTTAT
TGACCATTATTGACCACTCCCCTATTGGTGACGATACTTTCCATTACTAATCCAT
AACATGGCTCTTTGCCACAACTCTCTTTATTGGCTATATGCCAATACACTGTCCT
TCAGAGACTGACACGGACTCTGTATTTTTACAGGATGGGGTCTCATTTATTATTT
ACAAATTCACATATACAACACCACCGTCCCCAGTGCCCGCAGTTTTTATTAAACA
TAACGTGGGATCTCCACGCGAATCTCGGGTACGTGTTCCGGACATGGGCTCTT
CTCCGGTAGCGGCGGAGCTTCTACATCCGAGCCCTGCTCCCATGCCTCCAGCG
ACTCATGGTCGCTCGGCAGCTCCTTGCTCCTAACAGTGGAGGCCAGACTTAGG
CACAGCACGATGCCCACCACCACCAGTGTGCCGCACAAGGCCGTGGCGGTAG
GGTATGTGTCTGAAAATGAGCTCGGGGAGCGGGCTTGCACCGCTGACGCATTT
GGAAGACTTAAGGCAGCGGCAGAAGAAGATGCAGGCAGCTGAGTTGTTGTGT
TCTGATAAGAGTCAGAGGTAACTCCCGTTGCGGTGCTGTTAACGGTGGAGGGC
AGTGTAGTCTGAGCAGTACTCGTTGCTGCCGCGCGCGCCACCAGACATAATAG
CTGACAGACTAACAGACTGTTCCTTTCCATGGGTCTTTTCTGCAGTCACCGTCG
TCGACACGTGTGATCAGATATCGCGGCCGCTCTAGACCAGGCGCCTG
GATCCAGATCTGCTGTGCCTTCTAGTTGCCAGCCATCTGTTGTTTGCCCCTCC
CCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGT
GGGGTGGGGCAGCACAGCAAGGGGGAGGATTGGGAAGACAATAGCAGGCAT
GCTGGGGATGCGGTGGGCTCTATGGGTACCCAGGTGCTGAAGAATTGACCCG
GTTCCTCCTGGGCCAGAAAGAAGCAGGCACATCCCCTTCTCTGTGACACACCCT
GTCCACGCCCCTGGTTCTTAGTTCCAGCCCCACTCATAGGACACTCATAGCTCA
GGAGGGCTCCGCCTTCAATCCCACCCGCTAAAGTACTTGGAGCGGTCTCTCCC
TCCCTCATCAGCCCACCAAACCAAACCTAGCCTCCAAGAGTGGGAAGAAATTAA
AGCAAGATAGGCTATTAAGTGCAGAGGGAGAGAAAATGCCTCCAACATGTGAG
GAAGTAATGAGAGAAATCATAGAATTTCTTCCGCTTCCTCGCTCACTGACTCGC
TGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGG

FIG. 10A

TGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTATCTCAG
TTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTT
AAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGAC
AGTTACCAATGCTTAATCAGTGAGGCACCTATCTCAGCGATCTGTCTATTTCGTT
CATCCATAGTTGCCTGACTCCGGGGGGGGGGGGCGCTGAGGTCTGCCTCGTG
AAGAAGGTGTTGCTGACTCATACCAGGCCTGAATCGCCCCATCATCCAGCCAG
AAAGTGAGGGAGCCACGGTTGATGAGAGCTTTGTTGTAGGTGGACCAGTTGGT
GATTTTGAACTTTTGCTTTGCCACGGAACGGTCTGCGTTGTCGGGAAGATGCGT
GATCTGATCCTTCAACTCAGCAAAAGTTCGATTTATTCAACAAAGCCGCCGTCC
CGTCAAGTCAGCGTAATGCTCTGCCAGTGTTACAACCAATTAACCAATTCTGAT
TAGAAAAACTCATCGAGCATCAAATGAAACTGCAATTTATTCATATCAGGATTAT
CAATACCATATTTTTGAAAAAGCCGTTTCTGTAATGAAGGAGAAAACTCACCGA
GGCAGTTCCATAGGATGGCAAGATCCTGGTATCGGTCTGCGATTCCGACTCGT
CCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCAC
TCGCATCAACCAAACCGTTATTCATTCGTGATTGCGCCTGAGCGAGACGAAATA
CGCGATCGCTGTTAAAAGGACAATTACAAACAGGAATCGAATGCAACCGGCGC
AGGAACACTGCCAGCGCATCAACAATATTTTCACCTGAATCAGGATATTCTTCT
AATACCTGGAATGCTGTTTTCCCGGGGATCGCAGTGGTGAGTAACCATGCATC
ATCAGGAGTACGGATAAAATGCTTGATGGTCGGAAGAGGCATAAATTCCGTCA
GCCAGTTTAGTCTGACCATCTCATCTGTAACATCATTGGCAACGCTACCTTTGCC
ATGTTTCAGAAACAACTCTGGCGCATCGGGCTTCCCATACAATCGATAGATTGT
CGCACCTGATTGCCCGACATTATCGCGAGCCCATTTATACCCATATAAATCAGC
ATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCAT
GATGATATATTTTTATCTTGTGCAATGTAACATCAGAGATTTTGAGACACAACGT
GGCTTTCCCCCCCCCCCCATTATTGAAGCATTTATCAGGGTTATTGTCTCATGAG
CGGATACATATTTGAATGTATTTAGAAAAATAAACAAATAGGGGTTCCGCGCAC
ATTTCCCCGAAAAGTGCCACCTGACGTCTAAGAAACCATTATTATCATGACATTA
ACCTATAAAAATAGGCGTATCACGAGGCCCTTTCGTC

FIG. 10B nkCMVintBL Sequence

AAGCTTTTTTTGCAAAAGCCTAGGCCTCCAAAAAAGCCTCCTCACTACTTCTGG
AATAGCTCAGAGGCCGAGGCGGCCTCGGCCTCTGCATAAATAAAAAAAAT
TAGTCAGCCATGGGGCGGAGAATGGGCGGAACTGGGCGAAGTTAGGGGC
GGGATGGGCGGAGTGAATTATTGGCTATTGGCCATTGCATACGTTGTATCT
ATATCATAATATGTACATTTATATTGGCTCATGTCCAATATGACCGCCATGT
TGACATTGATTATTGACTAGTTATTAATAGTAATCAATTACGGGGTCATTAG
TTCATAGCCCATATATGGAGTTCCGCGTTACATAACTTACGGTAAATGGCC
CGCCTGCTGACCGCCCAACGACCCCCGCCCATTGACGTCAATAATGACGT
ATGTTCCCATAGTAACGCCAATAGGGACTTTCCATTGACGTCAATGGGTGG
AGTATTTACGGTAAACTGCCCACTTGGCAGTACATCAAGTGTATCATATGC
CAAGTCCGGCCCCCTATTGACGTCAATGACGGTAAATGGCCCGCCTGGCA
TTATGCCCAGTACATGACCTTACGGGACTTTGGTACTTGGCAGTACATCTA
CGTATTAGTCATCGCTATTACCATGGTGATGCGGTTTTGGCAGTACACCAA
TGGGCGTGGATAGCGGTTTGACTCACGGGGATTTCCAAGTCTCCACCCCA
TTGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTTG
GCTCTTATGCATGCTATACTGTTTTTGGCTTGGGGCCTATACACCCCCGCTC
CTTATGCTATAGGTGATGGTATAGCTTAGCCTATAGGTGTGGGTTATTGAC
CATTATTGACCACTCCCCTATTGGTGACGATACTTTCCATTACTAATCCATA
ACATGGCTCTTTGCCACAACTATCTCTATTGGCTATATGCCAATACTCTGTC
CTTCAGAGACTGACACGGACTCTGTATTTTTACAGGATGGGGTCCCATTTA
TTATTTACAAATTCACATATACAACAACGCCGTCCCCCGTGCCCGCAGTTTT
TATTAAACATAGCGTGGGATCTCCACGCGAATCTCGGGTACGTGTTCCGGA
CATGGGCTCTTCTCCGGTAGCGGCGGAGCTTCCACATCCGAGCCCTGGTC
CCATGCCTCCAGCGGCTCATGGTCGCTCGGCAGCTCCTTGCTCCTAACAGT
GGAGGCCAGACTTAGGCACAGCACAATGCCCACCACCACCAGTGTGCCGC
ACAAGGCCGTGGCGGTAGGGTATGTGTCTGAAAATGAGCTCGGAGATTGG
GCTCGCACCGTGACGCAGATGGAAGACTTAAGGCAGCGGCAGAAGAAGA
TGCAGGCAGCTGAGTTGTTGTATTCTGATAAGAGTCAGAGGTAACTCCCGT
TGCGGTTCTGTTAACGGTGGAGGGCAGTGTAGTCTGAGCAGTACTCGTTG
CTGCCGCGCGCGCCACCAGACATAATAGCTGACAGACTAACAGACTGTTC
CTTTCCATGGGTCTTTTCTGCAGTCACCGTCGTCGACCAGAGCTGAGATCC
TACAGGAGTCCAGGGCTGGAGAGAAAACCTCTGCGAGGAAAGGGAAGGA
GCAAGCCGTGAATTTAAGGGACGCTGTGAAGCAATCATGGATGCAATGAA
GAGAGGGCTCTGCTGTGTGCTGCTGCTGTGTGGAGCAGTCTTCGTTTCGC
CCAGCGCTAGAGGATCCAGATCTCTCGACATGGGCAAATATTATACGCAA
GGCGACAAGGTGCTGATGCCGCTGGCGATTCAGGTTCATCATGCCGTCTG
TGATGGCTTCCATGTCGGCAGAATGCTTAATGAATTACAACAGTACTGCGA
TGAGTGGCAGGGCGGGGCGTAATTTTTTTAAGGCAGTTATTGGTGCCCTTA
AACGCCTGGTGCTACGCCTGAATAAGTGATAATAAGCGGATGAATGGCAG
AAATTCGCCGGATCTTTGTGAAGGAACCTTACTTCTGTGGTGTGACATAAT
TGGACAAACTACCTACAGAGATTTAAAGCTCTAAGGTAAATATAAAATTTTT
AAGTGTATAATGTGTTAAACTACTGATTCTAATTGTTTGTGTATTTTAGATTC
CAACCTATGGAACTGATGAATGGGAGCAGTGGTGGAATGCCTTTAATGAG
GAAAACCTGTTTTGCTCAGAAGAAATGCCATCTAGTGATGATGAGGCTACT
GCTGACTCTCAACATTCTACTCCTCCAAAAAAGAAGAGAAAGGTAGAAGAC

FIG. 11A

CCCAAGGACTTTCCTTCAGAATTGCTAAGTTTTTTGAGTCATGCTGTGTTTA
GTAATAGAACTCTTGCTTGCTTTGCTATTTACACCACAAAGGAAAAAGCTG
CACTGCTATACAAGAAAATTATGGAAAAATATTCTGTAACCTTTATAAGTAG
GCATAACAGTTATAATCATAACATACTGTTTTTTCTTACTCCACACAGGCAT
AGAGTGTCTGCTATTAATAACTATGCTCAAAAATTGTGTACCTTTAGCTTTT
TAATTTGTAAAGGGGTTAATAAGGAATATTTGATGTATAGTGCCTTGACTA
GAGATCATAATCAGCCATACCACATTTGTAGAGGTTTTACTTGCTTTAAAAA
ACCTCCCACACCTCCCCCTGAACCTGAAACATAAAATGAATGCAATTGTTG
TTGTTAACTTGTTTATTGCAGCTTATAATGGTTACAAATAAAGCAATAGCAT
CACAAATTTCACAAATAAAGCATTTTTTTCACTGCATTCTAGTTGTGGTTTGT
CCAAACTCATCAATGTATCTTATCATGTCTGGATCGATCCCCGGGTACCGA
GCTCGAATTCGTAATCATGGTCATAGCTGTTTCCTGTGTGAAATTGTTATCC
GCTCACAATTCCACACAACATACGAGCCGGAAGCATAAAGTGTAAAGCCT
GGGGTGCCTAATGAGTGAGCTAACTCACATTAATTGCGTTGCGCTCACTGC
CCGCTTTCCAGTCGGGAAACCTGTCGTGCCAGCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
TCACTCAAAGGCGGTAATACGGTTATCCACAGAATCAGGGGATAACGCAG
GAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAA
CTCACGTTAAGGGATTTTGGTCATGAACAATAAAACTGTCTGCTTACATAAA
CAGTAATACAAGGGGTGTTATGAGCCATATTCAACGGGAAACGTCTTGCTC
GAGGCCGCGATTAAATTCCAACATGGATGCTGATTTATATGGGTATAAATG
GGCTCGCGATAATGTCGGGCAATCAGGTGCGACAATCTATCGATTGTATG
GGAAGCCCGATGCGCCAGAGTTGTTTCTGAAACATGGCAAAGGTAGCGTT
GCCAATGATGTTACAGATGAGATGGTCAGACTAAACTGGCTGACGGAATTT
ATGCCTCTTCCGACCATCAAGCATTTTATCCGTACTCCTGATGATGCATGGT
TACTCACCACTGCGATCCCCGGGAAAACAGCATTCCAGGTATTAGAAGAAT
ATCCTGATTCAGGTGAAAATATTGTTGATGCGCTGGCAGTGTTCCTGCGCC
GGTTGCATTCGATTCCTGTTTGTAATTGTCCTTTTAACAGCGATCGCGTATT
TCGTCTCGCTCAGGCGCAATCACGAATGAATAACGGTTTGGTTGATGCGA
GTGATTTTGATGACGAGCGTAATGGCTGGCCTGTTGAACAAGTCTGGAAA
GAAATGCATAAGCTTTTGCCATTCTCACCGGATTCAGTCGTCACTCATGGT
GATTTCTCACTTGATAACCTTATTTTTGACGAGGGGAAATTAATAGGTTGTA
TTGATGTTGGACGAGTCGGAATCGCAGACCGATACCAGGATCTTGCCATC
CTATGGAACTGCCTCGGTGAGTTTTCTCCTTCATTACAGAAACGGCTTTTTC
AAAAATATGGTATTGATAATCCTGATATGAATAAATTGCAGTTTCATTTGAT
GCTCGATGAGTTTTTCTAAGAATTCGCCATTCGCCATTCAGGCTGCGCAAC
TGTTGGGAAGGGCGATCGGTGCGGGCCTCTTCGCTATTACGCCAGCTGGC
GAAAGGGGGATGTGCTGCAAGGCGATTAAGTTGGGTAACGCCAGGGTTTT
CCCAGTCACGACGTTGTAAAACGACGGCCAGTGCC

```
Pst1          Sal1
CTGCAGTCACCGTCGTCGACCAGAGCTGAGATCCTACAGGAGTCCAGGGCTGG

AGAGAAAACCTCTGCGAGGAAAGGGAAGGAGCAAGCCGTGAATTTAAGGGAC

                   Met Asp Ala Met Lys Arg Gly Leu Cys Cys Val Leu Leu
GCTGTGAAGCAATCATGGATGCAATGAAGAGAGGGCTCTGCTGTGTGCTGCTG

Leu Cys Gly Ala Val Phe Val Ser Pro Ser Ala↓Arg BamH1 Bgl2
CTGTGTGGAGCAGTCTTCGTTTCGCCCAGCGCTAGAGGATCCAGATCTCTCGA
```

Arrow indicates the presumed site of signal peptide cleavage.

PCR PRIMERS:

FORWARD (SENSE) 5' GCCTTAGGTACCTGTAAGCAAAATGTTAGC 3'
                    {Kpn I site}{OspA HOMOLOGOUS SEQUENCE}

REVERSE (NON-SENSE) 5' TAATAATCTAGAAAAATTCTCCTTACTTAAGAGCGTTTTAAT 3'
                       {Xba I Site}                {Afl II Site}{OspA HOME. SEQ.}

FIG. 14

PCR PRIMERS:

Kpn I Site — OspB HOMOLOGOUS SEQUENCE

FORWARD (SENSE) 5' GCTTTAGGTACCTGTGCACAAAAAGGTGCT 3'

REVERSE (NON-SENSE) 5' AGGGGGGATCCTATATATTATTTTAAAGC 3'

Bam HI site — OspB HOMOLOGOUS SEQUENCE

FIG. 15

```
                                                          Pst I     TPA 5' UNTRANSLATED
  1  TAGCTGACAG ACTAACAGAC TGTTCCTTTC CATGGGTCTT TTCTGCAGTC ACCGTCGTCG
     ATCGACTGTC TGATTGTCTG ACAAGGAAAG GTACCCAGAA AAGACGTCAG TGGCAGCAGC

 61  ACCAGAGCTG AGATCCTACA GGAGTCCAGG GCTGGAGAGA AAACCTCTGC GAGGAAAGGG
     TGGTCTCGAC TCTAGGATGT CCTCAGGTCC CGACCTCTCT TTTGGAGACG CTCCTTTCCC
                                                          START TPA LEADER
121  AAGGAGCAAG CCGTGAATTT AAGGGACGCT GTGAAGCAAT CATGGATGCA ATGAAGAGAG
     TTCCTCGTTC GGCACTTAAA TTCCCTGCGA CACTTCGTTA GTACCTACGT TACTTCTCTC
                                                                Kpn 1 ospA
181  GGCTCTGCTG TGTGCTGCTG CTGTGTGGAG CAGTCTTCGT TTCGCCCAGC GGTACCTGTA
     CCGAGACGAC ACACGACGAC GACACACCTC GTCAGAAGCA AAGCGGGTCG CCATGGACAT
                                                            G  T  C pos 17
241  AGCAAAATGT TAGCAGCCTT GACGAGAAAA ACAGCGTTTC AGTAGATTTG CCTGGTGAAA
     TCGTTTTACA ATCGTCGGAA CTGCTCTTTT TGTCGCAAAG TCATCTAAAC GGACCACTTT

301  TGAAAGTTCT TGTAAGCAAA GAAAAAAACA AAGACGGCAA GTACGATCTA ATTGCAACAG
     ACTTTCAAGA ACATTCGTTT CTTTTTTTGT TTCTGCCGTT CATGCTAGAT TAACGTTGTC

361  TAGACAAGCT TGAGCTTAAA GGAACTTCTG ATAAAAACAA TGGATCTGGA GTACTTGAAG
     ATCTGTTCGA ACTCGAATTT CCTTGAAGAC TATTTTTGTT ACCTAGACCT CATGAACTTC
```

FIG. 16

```
  1  GTACTCGTTG CTGCCGCGCG CGCCACCAGA CATAATAGCT GACAGACTAA CAGACTGTTC
     CATGAGCAAC GACGGCGCGC GCGGTGGTCT GTATTATCGA CTGTCTGATT GTCTGACAAG
                    PstI        TPA 5' UNTRANSLATED
 61  CTTTCCATGG GTCTTTTCTG CAGTCACCGT CGTCGACCAG AGCTGAGATC CTACAGGAGT
     GAAAGGTACC CAGAAAAGAC GTCAGTGGCA GCAGCTGGTC TCGACTCTAG GATGTCCTCA

121  CCAGGGCTGG AGAGAAAACC TCTGCGAGGA AAGGGAAGGA GCAAGCCGTG AATTTAAGGG
     GGTCCCGACC TCTCTTTTGG AGACGCTCCT TTCCCTTCCT CGTTCGGCAC TTAAATTCCC
                         START TPA LEADER
181  ACGCTGTGAA GCAATCATGG ATGCAATGAA GAGAGGGCTC TGCTGTGTGC TGCTGCTGTG
     TGCGACACTT CGTTAGTACC TACGTTACTT CTCTCCCGAG ACGACACACG ACGACGACAC
                                 KpnI    ospB
241  TGGAGCAGTC TTCGTTTCGC CCAGCGGTAC CTGTGCACAA AAAGGTGCTG AGTCAATTGG
     ACCTCGTCAG AAGCAAAGCG GGTCGCCATG GACACGTGTT TTTCCACGAC TCAGTTAACC
                                 G    T    C  pos 16
301  TTCTCAAAAA GAAAATGATC TAAACCTTGA AGACTCTAGT AAAAAATCAC ATCAAAACGC
     AAGAGTTTTT CTTTTACTAG ATTTGGAACT TCTGAGATCA TTTTTTAGTG TAGTTTTGCG

361  TAAACAAGAC CTTCCTGCGG TGACAGAAGA CTCAGTGTCT TTGTTTAATG GTAATAAAAT
     ATTTCTTCTC CAACCACCCC ACTGTCTTCT GAGTCACAGA AACAAATTAC CATTATTTTA
```

COMPOSITIONS AND METHODS FOR ADMINISTERING BORRELIA DNA

RELATED APPLICATIONS

Reference is made to U.S. or PCT applications Ser. Nos. 08/320,416, filed Oct. 3, 1994 (allowed), 08/137,175, filed Oct. 26, 1993 (allowed), 08/262,220, filed Jun. 20, 1994, PCT/US95/07665, 08/373,455, filed Jan. 17, 1995 (abandoned), PCT/US92/08697, WO 90/04411, 08/470,672, filed Jun. 6, 1995 and 08/479,017 filed Jun. 6, 1995, each of which is hereby incorporated herein by reference. Several documents are cited in this application, with full citation thereof where cited, or in the listing headed "References" before the claims; and, each document cited herein is hereby incorporated herein by reference.

FIELD OF THE INVENTION

This invention relates to compositions and methods for administering Borrelia genospecies DNA encoding antigen (s) in vivo or in vitro. More particularly, this invention relates to compositions and methods for administering Borrelia genospecies DNA encoding an antigen or antigens, e.g., OspA (outer surface protein A) and/or OspB (outer surface protein B), and/or OspC (outer surface protein C), or fragments thereof, for expression thereof, in vivo, ex vivo or in vitro.

BACKGROUND OF THE INVENTION

Lyme disease is a multisystem illness, transmitted by ticks of the *Ixodes ricinus* complex. The spirochaete *Borrelia burgdorferi* sensu lato is the etiologic agent of Lyme disease, which is now the most common arthropod borne disease in the United States, and is endemic in Central Europe (Barbour and Fish 1993). More particularly, there are three genospecies of Borrelia associated with Lyme disease: *Borrelia burgdorferi, Borrelia afzelli* and *Borrelia garinii. Borrelia burgdorferi* is the etiologic agent of Lyme disease in North America, and some European Lyme disease is considered to be *Borrelia burgdorferi* sensu stricto. *Borrelia afzelli* and *Borrelia garinii* are the major cause of European Lyme disease and are considered *Borrelia burgdorferi* sensu lato.

Although Lyme disease is curable by antibiotic therapy in its early stages, if Lyme disease is allowed to progress, cardiac, neurological and joint abnormalities can arise. Investigations into the development of a human vaccine for Lyme disease are under way. The outer surface lipoprotein OspA of *Borrelia burgdorferi* is the current major candidate molecule for development of such a vaccine.

Recombinant OspA lipoprotein (rOspA) is known to elicit a protective immune response in mice against challenge by infectious *B. burgdorferi* (Fikrig et al., 1990; Erdile et al., 1993; U.S. Ser. No. 08/373,455). OspA is currently undergoing human field trials as a subcutaneously administered vaccine in the United States (Keller et al., 1994).

Above-cited applications 08/373,455 and PCT/US92/08697 relate to rOspA vaccines, especially lipidated rOspA, and methods for expressing DNA encoding OspA. Above-cited applications 08/320,416 and WO 90/04411 relate to DNA encoding OspA, the amino acid sequence of OspA, synthetic OspA, compositions containing OspA or synthetic OspA, and methods of using such compositions. And, the other above-cited applications relate to DNA encoding other Borrelia antigens or other Osps, or to DNA encoding useful fragments of OspA or of other Osps, amino acid sequences thereof, compositions containing such fragments or other Osps, and methods for using such compositions; and, such DNA that can be used in the methods of 08/373,455 or PCT/US92/08697 to produce OspA, other Borrelia antigens or outer surface proteins (Osps), or fragments thereof, can be used in this invention. In regard to DNA useful in this invention, reference is also made to Molecular Microbiology (1989), 3(4), 479–486, and PCT publications WO 93/04175, and WO 96/06165.

Alternative vaccination strategies are desirable as such provide alternative routes to administration or alternative routes to responses.

In particular, it is believed that heretofore the art has not taught or suggested administration to a eukaryotic cell in vitro or ex vivo, or to a mammalian host—domesticated or wild or human—susceptible to Lyme disease, of Borrelia genospecies DNA e.g., DNA encoding OspA and/or OspB, and/or OspC or expression thereof in vivo, especially as herein disclosed.

OBJECTS AND SUMMARY OF THE INVENTION

It is an object of the invention to provide methods and compositions for administering to a host, such as a mammalian host susceptible to Lyme Disease, Borrelia genospecies isolated and/or purified DNA encoding an antigen or antigens, e.g., isolated and/or purified DNA encoding an antigen or antigens from *Borrelia burgdorferi, Borrelia afzelli, Borrelia garinii* or combinations thereof, such as isolated and/or purified DNA encoding OspA, and/or OspB and/or OspC; for instance, DNA encoding *Borrelia burgdorferi* OspA and/or OspB and/or OspC. The compositions can include a carrier or diluent. The DNA is administered in a form to be expressed by the host, and preferably in an amount sufficient to induce a response such as a protective immune response; and, the DNA can be administered without any necessity of adding any immunogenicity-enhancing adjuvant.

Accordingly, the present invention provides Borrelia genospecies antigen DNA plasmids for expression by eukaryotic cells, compositions containing the plasmids, and methods for using the compositions and for using the products from the compositions.

The plasmid of the invention can comprise from upstream to downstream (5' to 3'): DNA encoding a promoter for driving expression in eukaryotic cells, DNA encoding a leader peptide for enabling secretion of a prokaryotic protein sequence from a mammalian cell, Borrelia genospecies antigen DNA, and DNA encoding a terminator.

The DNA encoding a promoter for driving expression in eukaryotic cells can be a eukaryotic, e.g., mammalian, viral promoter, such as a herpes virus promoter. A human cytomegalovirus promoter is presently preferred. The human cytomegalovirus promoter can be an immediate early human cytomegalovirus promoter such as HCMV-IE. The plasmid can contain the HCMV-IE gene 5' untranslated region (UTR) which includes Intron A. This sequence can be 3' to the HCMV-IE promoter and 5' to the portion of the chimeric 5' UTR sequence and leader peptide (the UTR and leader peptide coding sequence can be derived from the DNA encoding the human tissue plasminogen activator, as discussed below).

The DNA encoding a leader peptide is for facilitating secretion of a prokaryotic protein sequence from a mammalian cell. This DNA can be any DNA encoding a suitable or similar leader peptide for the purpose of secretion from a mammalian cell, e.g., DNA encoding a eukaryotic leader peptide. For instance, the DNA encoding a leader peptide can be from DNA encoding a peptide hormone, i.e., a peptide hormone leader peptide, such as from a mammal, e.g., a human peptide hormone leader peptide. Specific examples of DNA encoding leader peptides suitable use in the invention include the DNA encoding the leader peptide of insulin (human, bovine, porcine, etc.), renin, Factor VIII, and tissue plasminogen activator.

DNA encoding human tissue plasminogen activator (TPA) leader is presently preferred. The DNA encoding TPA is derived from the TPA gene and encodes a portion of the 5' UTR and leader peptide from the gene. TPA DNA having a portion of the 5' UTR and leader peptide can even increase eukaryotic cell expression. Without wishing to necessarily be bound by any one particular theory, increased expression can be due to the 5' UTR.

The Borrelia genospecies antigen DNA is preferably without the natural leader sequence. The Borrelia genospecies antigen DNA can preferably encode at least one antigen selected from OspA, OspB, OspC, OspD, other Osps, and other antigens (see applications cited under Related Applications). DNA without the natural leader sequence encoding OspA and/or OspB and/or OspC is presently preferred. The DNA can be from *Borrelia burgdorferi, Borrelia afzelli, Borrelia garinii* or from any combination thereof; with *Borrelia burdorferi* presently preferred.

The terminator can be any suitable terminator sequence for use in eukaryotic cells; for instance, a terminator sequence from a mamalian peptide hormone. The Bovine Growth Hormone (BGH) terminator is presently preferred.

The plasmid of the invention can contain genes for a fusion protein of the activator (e.g., TPA) and the Borrelia antigen (e.g., OspA, OspB, OspC).

The invention comprehends compositions comprising the plasmid and a carrier. The carrier can be any suitable carrier which does not disrupt the DNA or the function of the plasmid. Saline is a presently preferred carrier.

The invention further comprehends methods of using the compositions, e.g., administering the composition to a host susceptible to Lyme disease to elicit a response or express an antigen. The response can be protective. The response can be simply an antibody response, and the method can further include recovering antibodies and/or antibody-producing cells (with the cells further useful for producing hybridoma cells and monoclonal antibodies, e.g., by fusing the antibody-producing cells to produce hybridoma cells, and then obtaining monoclonal antibodies from expression by the hybridoma cells). The host can be a mammal, such as a human.

Still further, the invention provides methods for expressing an antigen or preparing an antigen in vitro comprising transfecting eukaryotic cells with the inventive plasmid. The method can further comprise recovering the antigen from the cells.

Methods for preparing the plasmid by ligating the respective pieces of DNA (DNA molecules) from which it is comprised, and methods for using the antibodies and antigens, as well as the antigens and antibodies themselves, are contemplated by the present invention.

Other objects and embodiments are disclosed or are obvious from the following Detailed Description.

BRIEF DESCRIPTION OF DRAWINGS

In the following Detailed Description, reference is made to the accompanying Figures, incorporated herein by reference, wherein:

FIGS. 2A, 2B, 2C, and 2D show the nucleotide sequence of VR2210 (SEQ ID NO:1) with the location of primer, used to amplify and insert the OspA coding sequence, underlined and overlined;

FIGS. 4A, 4B, 4C, and 4D show the nucleotide sequence of VR2211 (SEQ ID NO:2) with the location of primer, used to amplify and insect the OspB coding sequence, underlined and overlined;

FIGS. 5A, 5B, and 5C show the nucleotide sequence of ospA (TRH43; *B. burgdorferi* strain 31) (SEQ ID NO:3);

FIGS. 6A, 6B, and 6C show the nucleotide sequence of ospB (TRH46; *B. burgdorferi* strain B31) (SEQ ID NO:4);

FIGS. 7A, 7B, 7C, 7D, 7E, 7F, 7G, and 7H show a nucleotide sequence of ospA and ospB (SEQ ID NO:5) and a predicted amino acid sequence therefor (SEQ ID NO:18);

FIG. 9 shows the multiple cloning site sequence of VR1012 from nucleotides 1841 to 2001 (SEQ ID NO:6);

FIGS. 10A and 10B show the nucleotide sequence of VR1012 (SEQ ID NO:7);

FIGS. 11A and 11B show the nucleotide sequence of nkCMVintBL (SEQ ID NO:8);

FIG. 12 shows the nucleotide sequence of the nkCMVintBL cloning site with the TPA signal peptide sequence (SEQ ID NO:9);

FIG. 14 shows PCR primers for amplifying ospB (SEQ ID NO:12, 13);

FIG. 15 shows a partial nucleotide sequence of VR2210 (SEQ ID NO:16);

FIG. 16 shows a partial nucleotide sequence of VR2211 (SEQ ID NO:17);

DETAILED DESCRIPTION

Direct injection of plasmid DNA has become a simple and effective method of vaccination against a variety of infectious diseases (see, e.g., Science, 259:1745–49, 1993). It is potentially more potent and longer lasting than recombinant protein vaccination because it elicits both a humoral as well as a cellular immune response.

The present invention provides a DNA-based vaccine or immunological composition against Lyme disease (e.g., *Borrelia burgdorferi, afzelli*, or *garinii*) and can elicit an immunological response, which can confer protection, even up to 100%, in mice against challenge with an infectious strain of *Borrelia burgdorferi*. An exemplary plasmid of the invention contains the human cytomegalovirus immediate early promoter driving expression of the B31 outer surface protein A (OspA). To facilitate expression in eukaryotic cells, the natural leader sequence of the gene encoding OspA has been replaced with the human tissue plasminogen activator leader sequence.

Figure 17:
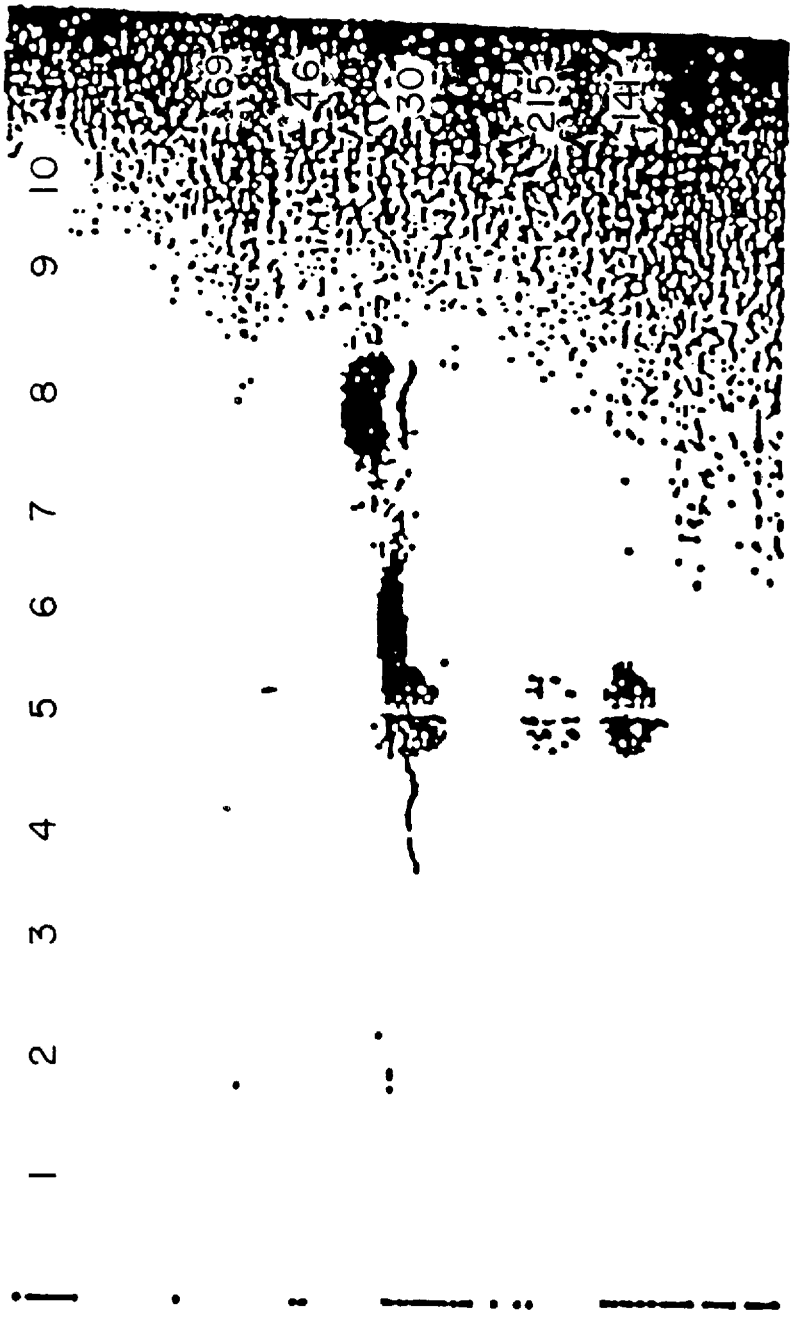
FIGS. 17, 18A and 18B show immunoblots.
Figure 18B:
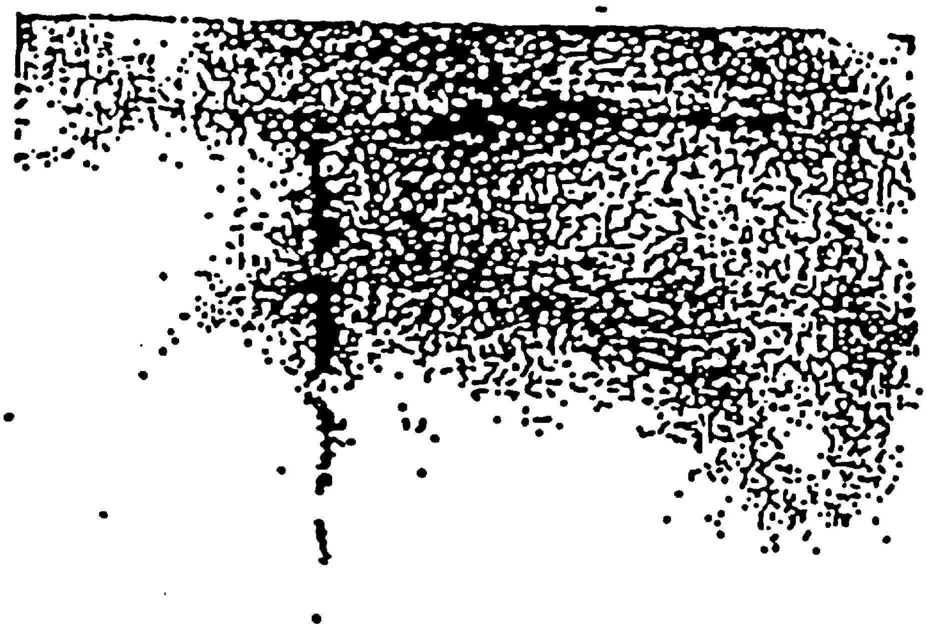
Figure 18A:
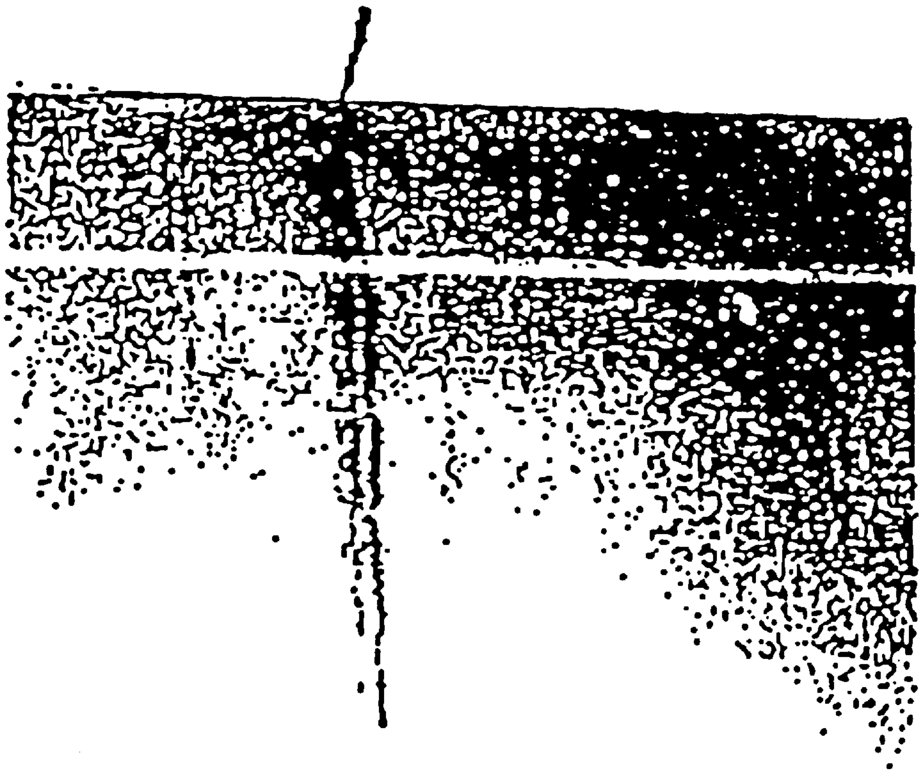

Expression and secretion was demonstrated in transiently transfected UM449 and BHK cells by Western blot (FIGS. 17, 18A, 18B).

Protection was demonstrated in C3H/HeN by injecting, intramuscularly, naked plasmid DNA and subsequently challenging with Sh2 spirochetes. Sera taken following vaccination contained high titers of antibody to OspA which inhibited spirochete growth in vitro. Immunized animals showed no sign of Lyme disease at 14 days after challenge. Moreover, all tissues examined were completely free of spirochetes.

Thus, a DNA vaccine or immunological composition, expressing a Borrelia antigen, for instance a *Borrelia burgdorferi, Borrelia afzelli, Borrelia garini* antigen or combinations thereof, e.g., OspA, OspB, OspC protein or any combination thereof, can protect mice against infection by a Borrelia genospecies, the etiologic agent of Lyme disease. The composition is thus useful for eliciting a protective response in a host susceptible to Lyme Disease, as well as for eliciting antigens and antibodies, which also are useful in and of themselves.

Therefore, as discussed above, the invention in a general sense preferably provides methods for immunizing, or vaccinating, or eliciting an immunological response in a host, such as a host susceptible to Lyme disease, e.g., a mammalian host, against Borrelia and accordingly Lyme Disease, by administering DNA encoding a Borrelia antigen, for instance DNA encoding a *Borrelia burgdorferi, Borrelia afzelli, Borrelia garinii* antigen or combinations thereof, e.g., OspA and/or OspB, and/or OspC, preferably OspA, in a suitable carrier or diluent, such as saline; and, the invention provides plasmids and compositions for performing the method, as well as methods for making the plasmids, and uses for the expression products of the plasmids, as well as for antibodies elicited thereby.

From present dog and human trials based on efficacy studies with mice (Erdile et al., 1993; U.S. Ser. No. 08/373, 455), it is clear that mice are now a suitable animal model with respect to Borrelia and Lyme disease for extrapolation to domestic animals, humans, and other animals susceptible to Lyme disease or Borrelia infection (e.g., wild animals such as deer).

In view of the broad nature of the invention, i.e., that the invention is applicable to Borrelia genospecies other than *burgdorferi* (i.e., the invention is also applicable to genospecies *afzelli* and *garinii*, and broadly to any Borrelia genospecies antigen or antigens and immunologically active fragments thereof), discussion herein directed to OspA is intended toward the broad nature of the invention, i.e., "OspA" is exemplary and can be read in this specification to include any Borrelia genospecies antigen or an immunological fragment thereof.

In the present invention, the DNA encoding OspA, or broadly, the Borrelia genospecies antigen or immunologically active fragment thereof, can be administered in dosages and by techniques well known to those skilled in the medical or veterinary arts taking into consideration such factors as the age, sex, weight, species and condition of the particular patient, and the route of administration. DNA encoding OspA, or broadly the Borrelia genospecies antigen or immunologically active fragment thereof, can be administered alone, or can be co-administered or sequentially administered with other Borrelia antigens, or with DNA encoding other Borrelia genospecies antigens; and, the DNA encoding OspA or broadly the Borrelia genospecies antigen or immunologically active fragment thereof, can be sequentially administered, e.g., each Spring as the "Lyme Disease season" is about to begin.

As broadly discussed above, the invention comprehends plasmids comprising DNA including Borrelia genospecies antigen DNA for expression by eukaryotic cells. The DNA, from upstream to downstream (5' to 3'), can comprise: DNA encoding a promoter for driving expression in eukaryotic cells, DNA encoding a leader peptide which enables secretion of a prokaryotic protein sequence from a mammalian cell, DNA encoding a Borrelia genospecies antigen (or antigens), and DNA encoding a terminator.

For instance, the promoter can be a eukaryotic viral promoter such as a herpes virus promoter, e.g., human cytomegalovirus promoter DNA.

The DNA encoding a leader peptide which enables secretion of a prokaryotic protein sequence from a mammalian cell is any DNA encoding any suitable leader for this purpose such as DNA encoding a eukaryotic, preferably mammalian, leader sequence; for instance, DNA encoding a leader peptide of a peptide hormone, or, for example, of insulin, renin, Factor VIII, TPA, and the like, with DNA encoding human tissue plasminogen activator (TPA) leader peptide presently preferred.

The human cytomegalovirus promoter can be an immediate early human cytomegalovirus promoteer such as HCMV-IE. As to HCMV promoter, reference is made to U.S. Pat. Nos. 5,168,062 and 5,385,839. The plasmid of the invention can contain the HCMV-IE gene 5' untranslated region (UTR) which includes Intron A. This sequence can be 3' to the HCMV-IE promoter and 5' to the activator portion of the 5' UTR sequence and leader peptide.

The TPA sequence can be derived from the TPA gene and can encode a portion of the 5' UTR and leader peptide from that gene. The 5' UTR of TPA may increase eukaryotic cell expression.

The Borrelia genospecies DNA can be from *B. burgdorferi, afzelli, garinii* or combinations thereof, e.g., *B. burgdorferi*; and, can encode an antigen such as OspA, OspB, OspC, OspD, other outer surface proteins or a combination of antigens, e.g., OspA and/or OspB and/or OspC; preferably without the natural leader sequence.

The transcriptional terminator sequence can be any suitable terminator, such as a eukaryotic terminator, for instance, DNA encoding a terminator for a mammalian peptide, with the BGH terminator presently preferred.

The plasmid can be in admixture with any suitable carrier, diluent or excipient such as sterile water, physiological saline, and the like. Of course, the carrier, diluent or excipient should not disrupt or damage the plasmid DNA.

The plasmid can be administered in any suitable manner. The plasmid can be in a composition suitable for the manner of administration. The compositions can include: liquid preparations for orifice, e.g., oral, nasal, anal, vaginal, peroral, intragastric administration and the like, such as solutions, suspensions, syrups, elixirs; and liquid preparations for parenteral, subcutaneous, intradermal, intramuscular, intravenous administration, and the like, such as sterile solutions, suspensions or emulsions, e.g., for administration by injection. Intramuscular administration and compositions therefor are presently preferred.

The plasmids of the invention can be used for in vitro expression of antigens by eukaryotic cells. Recovery of such antigens can be by any suitable techniques; for instance, techniques analogous to the recovery techniques employed in the documents cited herein (such as the applications cited under Related Applications and the documents cited therein).

The thus expressed antigens can be used in immunological, antigenic or vaccine compositions, with or without an immunogenicity-enhancing adjuvant ("expressed antigen compositions"). Such compositions can be administered in dosages and by techniques well known to those skilled in the medical or veterinary arts taking into consideration such factors as age, sex, weight, species, condition of the particular patient, and the route of administration. These compositions can be administered alone or with other compositions, and can be sequentially administered, e.g., each Spring as the "Lyme Disease season" is about to begin.

The route of administration for the expressed antigen compositions can be oral, nasal, anal, vaginal, peroral, intragastric, parenteral, subcutaneous, intradermal, intramuscular, intravenous, and the like.

The expressed antigen compositions can be solutions, suspensions, emulsions, syrups, elixirs, capsules (including "gelcaps"—gelatin capsule containing a liquid antigen or fragment thereof preparation), tablets, hard-candy-like preparations, and the like. The expressed antigen compositions may contain a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Suitable dosages for plasmid compositions and for expressed antigen compositions can also be based upon the examples below, and upon the documents herein cited. For example, suitable dosages can be 0.5–500 $\mu$g antigen, preferably 0.5 to 50 $\mu$g antigen, for instance, 1–10 $\mu$g antigen in expressed antigen compositions. In plasmid compositions, the dosage should be a sufficient amount of plasmid to elicit a response analogous to the expressed antigen compositions; or expression analogous to dosages in expressed antigen compositions. For instance, suitable quantities of plasmid DNA in plasmid compositions can be 0.1 to 2 mg, preferably 1–10 $\mu$g.

Thus, in a broad sense, the invention further provides a method comprising administering a composition containing plasmid DNA including DNA encoding a Borrelia genospecies antigen or antigens: for expression of the antigen or antigens in vivo for eliciting an immunological, antigenic or vaccine (protective) response by a eukaryotic cell; or, for ex vivo or in vitro expression (That is, the cell can be a cell of a host susceptible to Lyme Disease, i.e., the administering can be to a host susceptible to Lyme Disease such as a mammal, e.g., a human; or, the cell can be an ex vivo or in vitro cell). The invention further provides a composition containing a Borrelia genospecies antigen or antigens from expression of the plasmid DNA by a eukaryotic cell, in vitro or ex vivo, and methods for administering such compositions to a host mammal susceptible to Lyme disease to elicit a response.

Since the methods can stimulate an immune or immunological response, the inventive methods can be used for merely stimulating an immune response (as opposed to also being a protective response) because the resultant antibodies (without protection) are nonetheless useful. From eliciting antibodies, by techniques well-known in the art, monoclonal antibodies can be prepared and, those monoclonal antibodies, can be employed in well known antibody binding assays, diagnostic kits or tests to determine the presence or absence of a Borrelia genospecies or to determine whether an immune response to the bacteria has simply been stimulated. Those monoclonal antibodies can also be employed in recovery or testing procedures, for instance, in immunoadsorption chromatography to recover or isolate a Borrelia genospecies antigen such as OspA, OspB, or OspC.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

To prepare the inventive plasmids, the DNA therein is preferably ligated together to form a plasmid. For instance, the promoter, leader sequence, antigen and terminator DNA is preferably isolated, purified and ligated together in a 5' to 3' upstream to downstream orientation. A three-way ligation, as exemplified below, is presently preferred.

Accordingly, the inventive methods and products therefrom have several hereinstated utilities. Other utilities also exist for embodiments of the invention.

A better understanding of the present invention and of its many advantages will be had from the following examples given by way of illustration.

EXAMPLES

Example 1

Plasmid Construction

Figure 1:
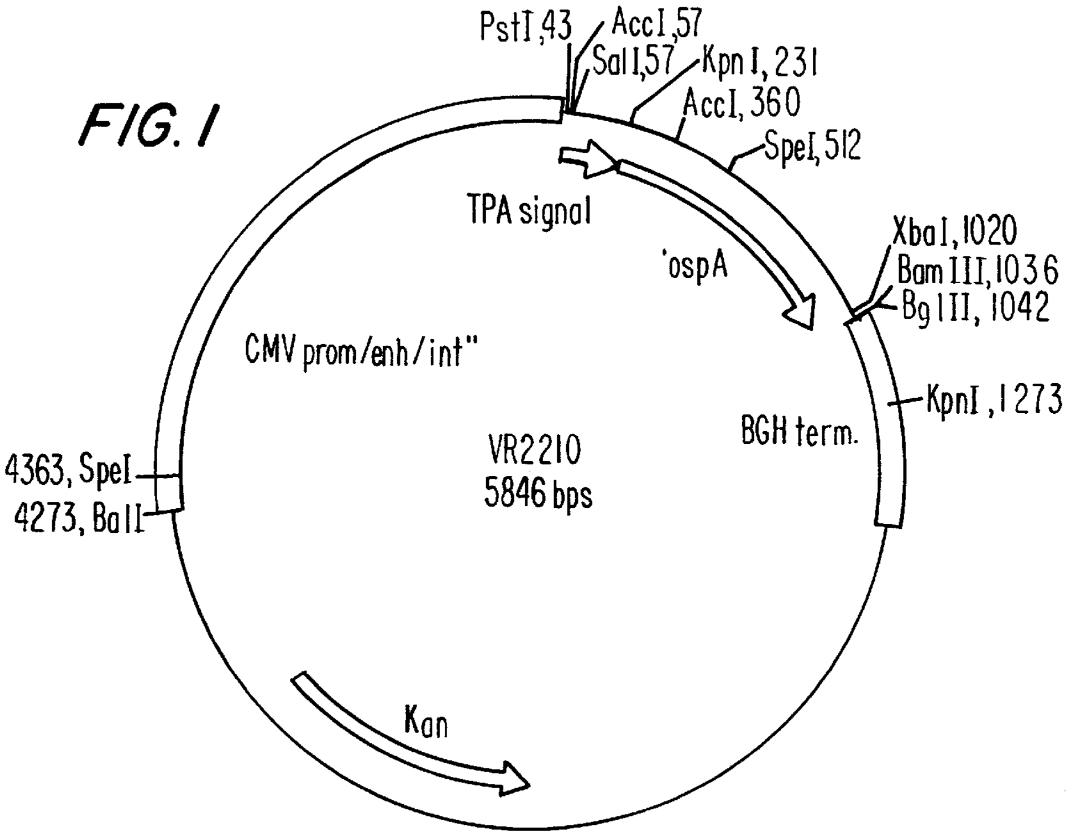
FIG. 1 shows a diagram of VR2210 with a few characteristic restriction sites.
Figure 3:
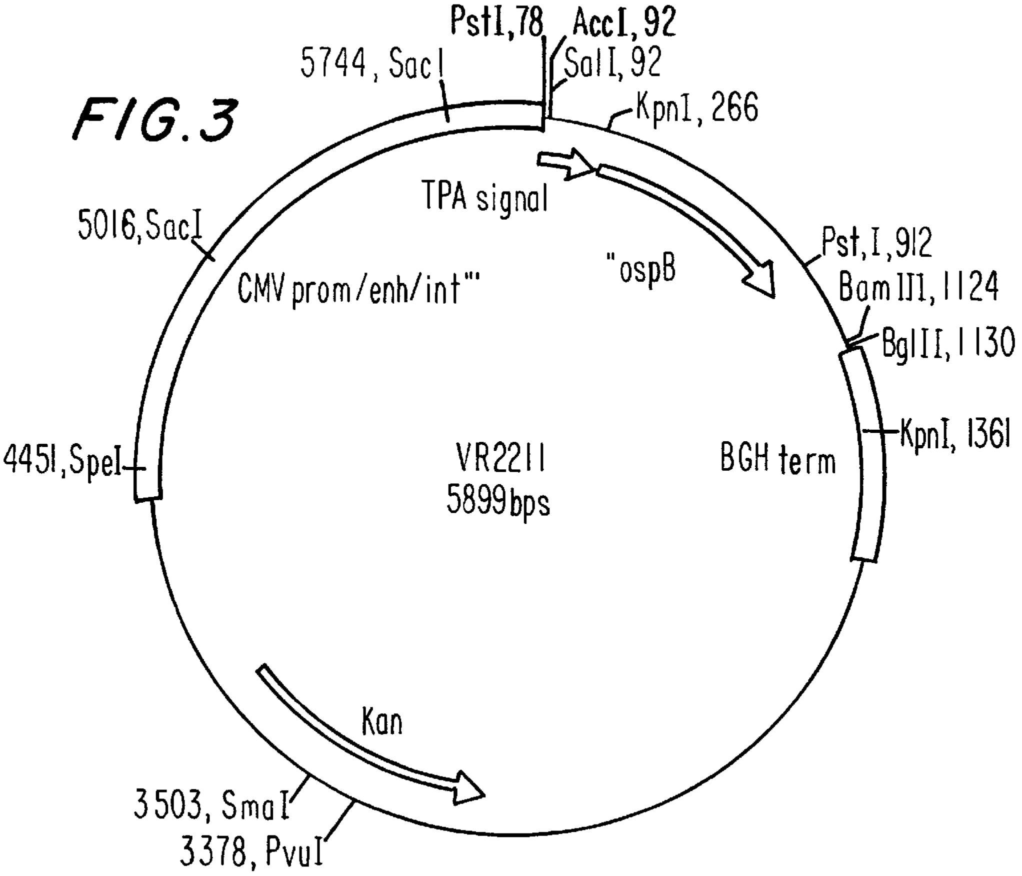
FIG. 3 shows a diagram of VR2211 with a few characteristic restriction sites.
Figure 8:
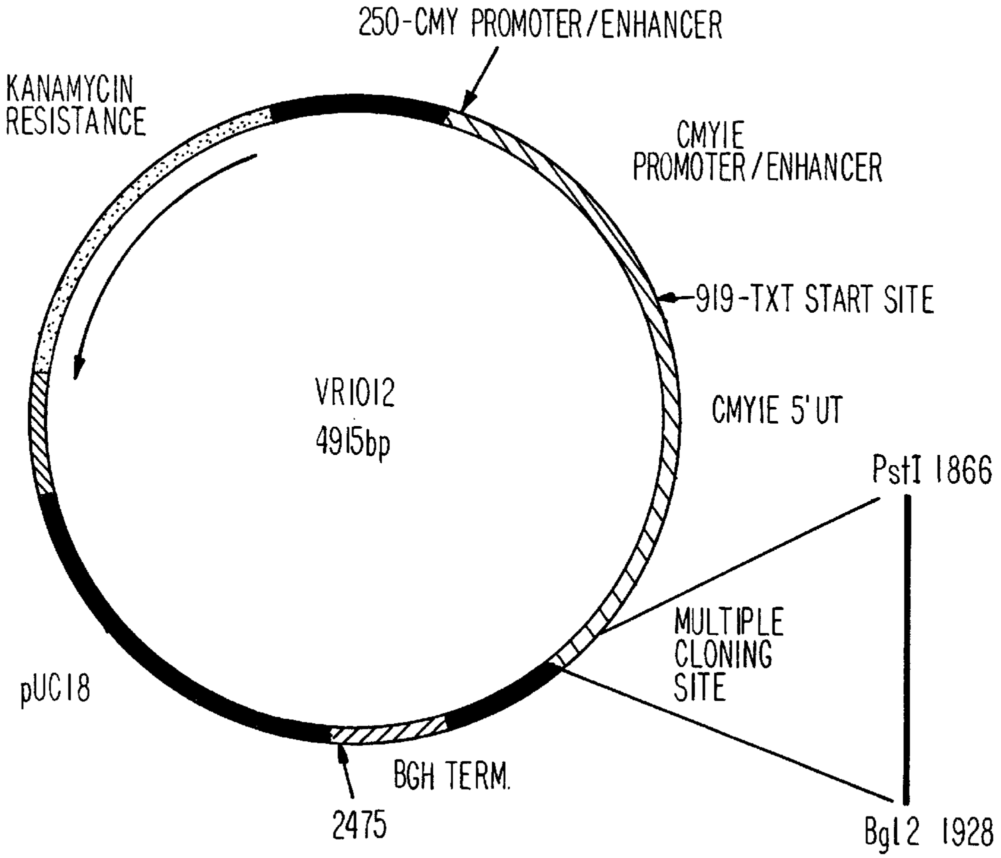
FIG. 8 shows a diagram of VR1012.
Figure 13:
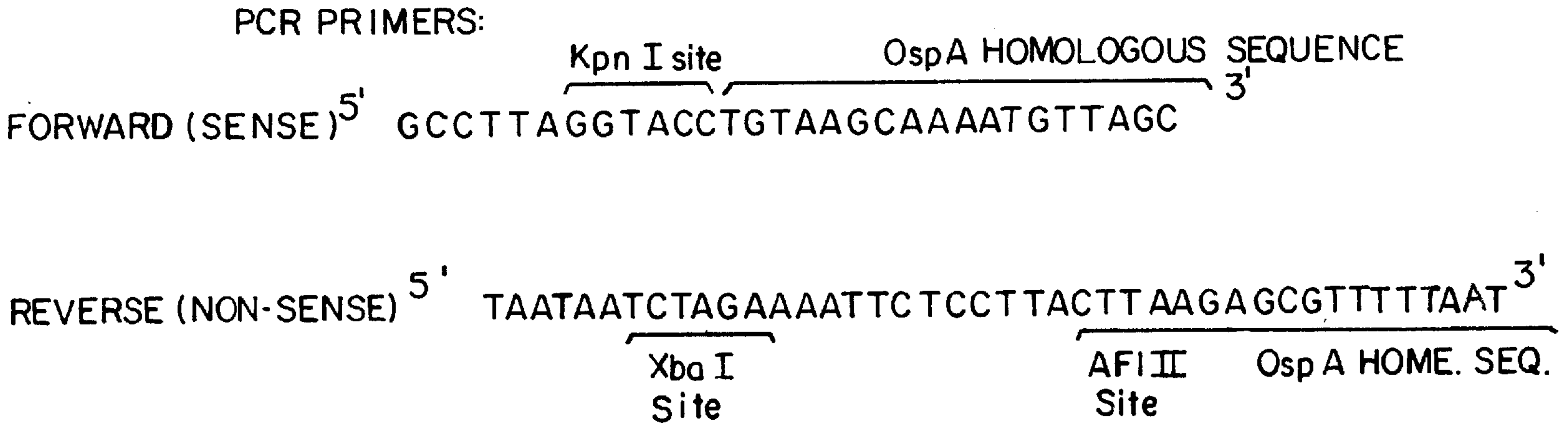
FIG. 13 shows PCR primers for amplifying ospA (SEQ ID NO:10, 11)

DNA plasmids VR2210 (FIGS. 1 and 2) (SEQ ID NO:1) and VR2211 (FIGS. 3 and 4) (SEQ ID NO:2) containing, respectively, genes coding for OspA (FIG. 5) (SEQ ID NO:3) and OspB (FIG. 6) (SEQ ID NO:4) from *Borrelia burgdorferi* (see FIG. 7) (SEQ ID NO:5) were constructed by isolating, individually, three DNA molecules: (1) a first DNA molecule having a DNA sequence from restriction endonuclease (PstI and XbaI) digested VR1012 plasmid (FIGS. 8, 9, 10) (SEQ ID NOS:6, 7); (2) a second DNA molecule having a DNA sequence from PCR amplified TPA 5' UTR and leader peptide coding sequence (from nkCMVintBL; see Manthorpe et al. (1993) Human Gene Therapy 4, 419–431; see also Chapman et al. (1991) Nucleic Acids Research 19, 3979–86), PstI and KpnI digested (subsequent to PCR amplification) (FIGS. 11, 12) (SEQ ID NOS:8, 9); and (3) a third DNA molecule having a DNA sequence from PCR amplified Borrelia antigen coding sequence, KpnI and XbaI digested, e.g., PCR amplified DNA encoding OspA (FIG. 5; SEQ ID NO:3) (PCR primers: FIG. 13; SEQ ID NOS:10, 11) or OspB (FIG. 6; SEQ ID NO:5) (PCR primers: FIG. 14; SEQ ID NOS:12, 13) (see also FIG. 7; SEQ ID NO:5; and Howe et al., 1986, Infection and Immunity 54:207–212 ("Howe et al. 1986"); Berstrom et al., 1989, Molecular Microbiology, 3(4), 479–486). The natural leader sequences of the DNA encoding the Borrelia antigen is not present so as to facilitate expression and secretion in mammalian cells. The constructs (VR2210, VR2211) express secreted proteins in vitro and elicit a specific antibody response in vivo.

In particular, the construct VR2210 contains DNA encoding OspA and was made by ligating three aforementioned DNA molecules (fragments) together (wherein the third DNA molecule or sequence in the foregoing paragraph is DNA encoding OspA, from a plasmid as in Howe et al. 1986, e.g., pTRH43); and, the construct VR2211 contains DNA encoding OspB and was made by ligating the three aforementioned DNA fragments together (wherein the third DNA molecule or sequence in the foregoing paragraph is DNA encoding OspB from a plasmid as in Howe et al., 1986, e.g., pTRH46).

More specifically, the DNA for encoding TPA 5' UTR and leader peptide, ospA and ospB were PCR amplified. The TPA signal was PCR amplified from plasmid nKCMVintBL using the following primers:

PstI (CTG|CAG) (SEQ ID NO:14)

TPA5' - TCT|TTT|CTG|CAG|TCA|CCG|TCG

XbaI (AGA|TCT), BamHI (GGA|TCC), KpnI (GGT|ACC) (SEQ ID NO:15)

TPA3' - GAG|AGA|TCT|GGA|TCC|GGT|ACC|GCT|GGG|CGA|AAC|GAA

The ospA gene was PCR amplified from pTRH43 using the primers shown in FIG. 13 (SEQ ID NOS:10, 11) ("Forward" is ospA 5' primer and "Reverse" is ospA 3' primer). The ospB gene was PCR amplified from pTRH46 using the primers shown in FIG. 14 (SEQ ID NOS:12, 13) ("Forward" is ospB 5' primer and "Reverse" is ospB 3' primer).

PCR program:

1st—Anneal primer and template
1. 94° C., 2 minutes
2. Ramp slowly, 10 minutes, down to 45° C.
3. 45° C., 5 minutes 2nd—Cycle program
1. 72° C., 3'
2. 93° C., 1' 30"
3. Go to 1 32 cycles
4. 54° C., 2' 30"
5. 72° C. 10'
6. 4° C. 24 hours

PCR REACTIONS

| $H_2O$ | BUF-FER | dNTPs | 5' PRIMER | 3' PRIMER | DNA | Taq |
|---|---|---|---|---|---|---|
| 82 uL | 10 uL Taq | 3 uL (25 mM) | TPA-5' 2 uL (25 pico mole/uL) | TPA-3' 2 uL (25 pico mole/mM) | ∅ | 1 uL |
| 80 uL | 10 uL Taq | 3 uL (25 mM) | 2 uL (25 pico mole/uL) | 2 uL (25 pico mole/mM) | 2 uL (5 pico mole/uL) | 1 uL |
| | 10 uL Taq | 3 uL (25 mM) | 2 uL (25 pico mole/uL) | 2 uL (25 pico mole/mM) | 2 uL (5 pico mole/uL) | 1 uL |
| | 10 uL Taq | 3 uL (25 mM) | 2 uL (25 pico mole/uL) | 2 uL (25 pico mole/mM) | 2 uL (5 pico mole/uL) | 1 uL |
| 82 uL | 10 uL Taq | 3 uL (25 mM) | ospA - 5' 2 uL (25 pico mole/uL) | ospA - 3' 2 uL (25 pico mole/uL) | ∅ | 1 uL |
| 80 uL | 10 uL Taq | 3 uL (25 mM) | ospA - 5' 2 uL (25 pico mole/uL) | ospA - 3' 2 uL (25 pico mole/uL) | 2 uL (5 pico mole/uL) | 1 uL |

-continued

PCR REACTIONS

| $H_2O$ | BUF-FER | dNTPs | 5' PRIMER | 3' PRIMER | DNA | Taq |
|---|---|---|---|---|---|---|
| 72 uL | 10 uL Taq | 3 uL (25 mM) | ospA - 5' 2 uL (25 pico mole/uL) | ospA - 3' 2 uL (25 pico mole/uL) | 10 uL (1 pico mole/uL) | 1 uL |
| 82 uL | 10 uL Taq | 3 uL (25 mM) | ospB - 5' 2 uL (25 pico mole/uL) | ospB - 3' 2 uL (25 pico mole/uL) | ∅ | 1 uL |
| 80 uL | 10 uL | 3 uL | ospB - 5' | ospB - 3' | 2 uL (5 pico | 1 uL |

-continued

PCR REACTIONS

| $H_2O$ | BUF-FER | dNTPs | 5' PRIMER | 3' PRIMER | DNA | Taq |
|---|---|---|---|---|---|---|
| | Taq | (25 mM) | 2 uL (25 pico mole/uL) | 2 uL (25 pico mole/uL) | mole/uL) | |
| 72 uL | 10 uL Taq | 3 uL (25 mM) | ospB - 5' 2 uL (25 pico mole/uL) | ospB - 3' 2 uL (25 pico mole/uL) | 10 uL (1 pico mole/uL) | 1 uL |

The ospA PCR fragments were digested with KpnI/XbaI as follows:

| | | |
|---|---|---|
| A. Mixed: | 72 uL | ospA |
| | 10 uL | NEB Buffer #1 (New England Biolabs ("NEB") Buffer #1) |
| | 10 uL | 10x BSA (Bovine serum albumin) |
| | 8 uL | KpnI (10 ug/uL) (10 units/uL) |
| | 100 uL | total. |

The mixture was allowed to sit for 2 hrs at 37° C. and then subjected to benzene/$CHI_3$ extraction and spin column (G-50 Sephadex) for purification.

| | | |
|---|---|---|
| B. Mixed: | 100 uL | DNA (5 ug) (from A.) |
| | 11.5 uL | NEB Buffer #2 (New England Biobbs ("NEB") Buffer #2) |
| | 1 uL | BSA 100x |
| | 4 uL | XbaI (20 g/uL) (20 units/uL) |
| | 115 uL | total. |

The mixture was allowed to sit for 2 hrs at 37° C.

QIAquick (Qiagen) columns were used to purify the fragments (Final volume=50 $\mu$L in 10 mM Tris, pH 8.5).

The TPA fragments were digested with PstI/KpnI as follows:

| | | |
|---|---|---|
| A. Mixed: | 20 uL | TPA (in Tris pH 8.5) |
| | 10 uL | NEB Buffer #1 |
| | 1 uL | 100x BSA |
| | 64 uL | TE (10 mM Tris, 1 mM EDTA, pH 8.0) |
| | 5 uL | KpnI (10 ug/uL) (10 units/uL) |
| | 100 uL | total. |

The mixture was allowed sit for 2 hrs at 37° C. and then subjected to QIAquick DNA spin column; and eluted with 50 $\mu$L $H_2O$ (and then subject to B).

| | | |
|---|---|---|
| B. Mixed: | 50 uL | TPA (from A.) |
| | 6 uL | NEB Buffer #3 (New England Biolabs ("NEB") Buffer #3) |
| | 2 uL | PstI (10 units/uL) |
| | 2 uL | TE |
| | 60 uL | total. |

The mixture was let sit 2 hrs at 37° C. Thereafter 40 $\mu$L TE was added; and then subjected to phenol/chloroform extraction (1X). After extraction the mixture was subjected to G-50 spin column to purify.

The ospB PCR reaction products that were uncut were gel purified by ethanol precipitation, resuspended, loaded on a 1% TBE (Tris-borate) mini-gel and then gel purified using a QIAEX procedure as follows:

1. Excise bands and weigh.
2. Add 3 $\mu$L/mg of gel slice.
3. Vortex QIAEX 1' to completely resuspend.
4. Add 10 $\mu$L QIAEX for every 5 $\mu$g DNA or less Vortex.
5. Incubate at 50° C. for 10' mix every 2 minutes.
6. Centrifuge for 30".
7. Wash 2X in QX2; 500 $\mu$L wash. Resuspend by vortexing. Spin 30" full speed.
8. Wash 2X in QX3; 500 $\mu$L wash.
9. Remove all traces of supernatant after last wash.
10. Allow to air dry 15 minutes.
11. Elute with 20 $\mu$L TE. Resuspend. Incubate 5' at room temperature and spin down QIAEX. Remove supernatant.

The ospB fragments were digested with KpnI/BamHI as follows:

| | | |
|---|---|---|
| A. Mixed: | 5uL | TE (1.3 ug) |
| | 33uL | ospB (⅓ ug) |
| | 5uL | NEB Buffer #1 |
| | 5uL | 10X BSA |
| | 2uL | KpnI (10 ug/uL) |
| | 50 uL | total. |

The mixture was let sit for 2 hrs at 37° C. Thereafter the mixture was cleaned with Quiaquick and subjected to a spin column.

| | | |
|---|---|---|
| B. Mixed: | 30 uL | DNA (1.3 mg; from A.) |
| | 4 uL | BamHI Buffer (New England Biolabs) |
| | 1 uL | BamHI (20 ug/uL) (20 units/uL) |
| | 5 uL | TE |
| | 40 uL | total. |

The mixture was let sit 2 hrs at 37° C. Thereafter the mixture was subjected to a QIAquick column, cleaned and eluted in 30 $\mu$L $H_2O$.

VR1012 was digested with XbaI/PstI as follows:

| | | |
|---|---|---|
| A. Mixed: | 5uL | DNA (5 ug) VR1012 |
| | 3uL | 10X BSA |
| | 3uL | NEB Buffer #2 |
| | 18 uL | TE |
| | 1 uL | XbaI |
| | 30 uL | total. |

The mixture was let sit for 2 hrs at 37° C. 1 $\mu$L was then removed for gel analysis which confirmed digestion.

| B. Added to product of A: | |
|---|---|
| 1.5 uL | 1M Tris |
| 3.5 uL | NaCl (500 mM) |
| 1 uL | PstI |
| 35 uL | Total |

The mixture in B. was let sit for 2 hours at 37° C. Thereafter, 1 $\mu$L of EcoRV was added and the resultant mixture incubated at 37° C. for an additional hour (this cuts the small restriction fragment in half and can increase efficiency of removal by the spin column). The mixture was then subjected to a G50 spin column to remove the small insert.

To then construct VR2210, a mixture containing 1 $\mu$L of the VR1012 digested DNA (25 ng), 1 $\mu$L of the digested ospA DNA (200 ng), 6 $\mu$L of the digested TPA DNA (50 ng), 2 $\mu$L NEB Buffer #2, 10 $\mu$L NEB Buffer #1, and 1 $\mu$L ligase (Boehringer Mannheim) was prepared. To construct VR2211, a mixture containing 1 $\mu$L of the VR1012 digested DNA (25 ng), 5 $\mu$L of the digested ospB DNA (150 ng), 3 $\mu$L of the digested TPA DNA, 2 $\mu$L NEB Buffer #2, 10 $\mu$L NEB Buffer #1, and 1 $\mu$L of ligase (Boehringer Mannheim) was prepared. Rapid, 3-way ligations occurred in each of the mixtures, with VR2210 and VR2211 resulting, respectively. Control mixtures without (i) the ospA and TPA DNA and (ii) the ospB and TPA were also prepared. The control mixtures were set up to test for the number of background clones due to uncut vector. A very low number (less than one-tenth) of clones were detected as a result of these control ligations clearly indicating that the three-way ligations worked efficiently.

FIG. 15 provides a partial sequence of VR2210 extending from a position 5' to PstI site to an arbitrary point 3' to the KpnI site (KpnI, 231) (through the PstI site, the TPA leader, the KpnI site, and into the ospA DNA) (SEQ ID NO: 16). FIG. 16 provides a partial sequence of VR2211 extending from a position 5' to PstI site to an arbitrary point 3' to the KpnI site (KpnI, 266) (through the PstI site, the TPA leader, the KpnI site and into the ospB DNA) (SEQ ID NO: 17).

ANALYTICAL RESTRICTION DIGEST:

| Enzyme(s) | Number and size of fragments |
|---|---|
| VR2210 | |
| 1. KpnI | 2 fragments: 1042/4804 |
| 2. HindIII | 2 fragments: 2803/3043 |
| 3. PstI | 2 fragments: 783/5063 |

-continued

| ANALYTICAL RESTRICTION DIGEST: | |
|---|---|
| Enzyme(s) | Number and size of fragments |
| | VR2211 |
| 1. KpnI | 2 fragments: 1091/4803 |
| 2. HindIII | 2 fragments: 2460/3439 |
| 3. PstI | 2 fragments: 834/5065 |

FIG. 7 provides the nucleotide sequence (SEQ ID NO: 5) of the ospA and ospB genes and the predicted amino acid sequences (SEQ ID NO: 18) of OspA and OspB. Numbers above each line refer to amino acid positions, whereas numbers below the sequence refer to nucleotide positions. The promoter regions P1 and P2 are indicated by horizontal lines. The respective −35 and −10 regions are also shown. The ribosomal binding sites (RBS) are shown by a horizontal line and bold lettering. A possible stem and loop structure at the end of the ospB sequence is indicated by horizontal broken arrows. Start codons of respective OspA and OspB proteins are indicated and stop codons are marked by asterisks. FIG. 7 also shows the location of the KpnI, XbaI and BamHI sites, with arrows indicating direction (first KpnI to XbaI for OspA DNA, second KpnI to BamHI for OspB DNA are also indicated).

Example 2

Transfections

5 μg of VR2210 was transfected into both BHK and UM449 human melanoma cells (from Mark Cameron, Univ. Mich.) cells according to the protocol of Felgner et al. (1994), J. Biol. Chem. 269, 2550–2561. The resultant supernatant and cell extract were analyzed for expression of OspA by Western blot, using two anti-OspA antibodies, 3TS at 1:100 dilution and H5332 at 1:10 dilution in 5% milk/BBS (as to the antibodies, reference is made to Barbour, A. G. et al., J. Infect. Dis. 1985, 152, 478–84; Barbour et al., Infect Immun. 1983, 41, 795–804).

As the Western blot (FIG. 17) shows, UM449 cells give a higher level of expression of OspA than BHK cells. Also, there is more OspA in the culture supernatant than in the cell lysate. Therefore, the prokaryotic protein is efficiently transported out of the mammalian cells by a eukaryotic signal peptide sequence (TPA). A summary of the results shown in FIG. 17 is provided by the following tabulation.

| Gel lane | Sample | Cells | sup/ extract | DNA Conc. | DNA/ lipid | Amt. loaded |
|---|---|---|---|---|---|---|
| 1 | VR2211* | UM449 | extract | 5 ug | 1/1 | 40 ul |
| 2 | VR2210 | UM449 | extract | 5 ug | 1/1 | 40 ul |
| 3 | VR2211 | BHK | extract | 5 ug | 1/1 | 40 ul |
| 4 | VR2210 | BHK | extract | 5 ug | 1/1 | 40 ul |
| 5 | MW marker | | | | | 15 ul |
| 6 | pos control | | B31 lysate | | | 1 ul |
| 7 | VR2211 | UM449 | sup | 5 ug | 1/1 | 20 ul |
| 8 | VR2210 | UM449 | sup | 5 ug | 1/1 | 20 ul |
| 9 | VR2211 | BHK | sup | 5 ug | 1/1 | 20 ul |
| 10 | VR2210 | BHK | sup | 5 ug | 1/1 | 20 ul |

*VR2211 is a plasmid containing the OspB gene and is used as a negative control on the Western.

This Example also demonstrates that the inventive Borrelia antigen DNA plasmid compositions are additionally useful for in vitro expression of antigen(s) (which by themselves are useful, e.g., for preparing antigenic, immunological or vaccine compositions, or for diagnostic, detection or assay purposes). Example 3

Transfections

5 μg of VR2211 was transfected into UM449 human melanoma cells according to the protocol of Felgner et al. (1994), J. Biol. Chem. 269, 2550–2561. Supernatants and cell extracts were analyzed for expression of OspB by Western blot using a monoclonal anti-OspB called H68 and by a monoclonal anti-OspB called H6831 (as to the antibodies, reference is made to Barbour et al., Infect. Immun. 1984, 45, 94–100) (FIGS. 18A and 18B) with the anti-OspB H68 and H6831 at 1:10 in Blotto. These antibodies detect OspB in both supernatants and cell extracts. The monoclonal anti-OspB designated H6831 binds to spirochete OspB (strain B31) and to unmodified OspB (in vitro translated) but not to modified OspB (i.e., glycosylated and/or phosphorylated by mammalian cellular machinery). Possibly the epitope for H6831 is blocked by eukaryotic post-translational modifications.

A summary of the results shown in FIG. 18A is provided by the following tabulation.

| Lane | Sample | Cells | sup/ extract | DNA Conc. | DNA/ lipid | Amt. loaded |
|---|---|---|---|---|---|---|
| 1 | B31 | spirochete | lysate | | | 1 ul |
| 2 | MW markers | | | | | 15 ul |
| 3 | VR2211 clone #16 | UM449 | extract | 5 ug | 1/1 | 40 ul |
| 4 | no DNA | UM449 | extract | | all lipid | 40 ul |
| 5 | VR2210 | UM449 | extract | 5 ug | 1/1 | 40 ul |
| 6 | VR2211 clone #1 | UM449 | extract | 5 ug | 1/1 | 40 ul |
| 7 | VR2211 clone #2 | UM449 | extract | 5 ug | 1/1 | 40 ul |
| 8 | VR2211 clone #3 | UM449 | extract | 5 ug | 1/1 | 40 ul |
| 9 | VR2211 clone #4 | UM449 | extract | 5 ug | 1/1 | 40 ul |
| 10 | VR2211 clone #5 | UM449 | extract | 5 ug | 1/1 | 40 ul |

A summary of the results shown in FIG. 18B is provided by the following tabulation.

| Lane | Sample | Cells | Supernatant | DNA Conc. | DNA/lipid | Amt. loaded |
|---|---|---|---|---|---|---|
| 1 | B31 | spiro-chete | lysate | | | 1 ul |
| 2 | MW markers | | | | | 15 ul |
| 3 | VR2211 #16 | UM449 | sup. | 5 ug | 1/1 | 20 ul |
| 4 | no DNA | UM449 | sup. | | all lipid | 20 ul |
| 5 | VR2210 | UM449 | sup | 5 ug | 1/1 | 20 ul |
| 6 | VR2211 #1 | UM449 | sup. | 5 ug | 1/1 | 20 ul |
| 7 | VR2211 #2 | UM449 | sup. | 5 ug | 1/1 | 20 ul |
| 8 | VR2211 #3 | UM449 | sup. | 5 ug | 1/1 | 20 ul |
| 9 | VR2211 #4 | UM449 | sup. | 5 ug | 1/1 | 20 ul |
| 10 | VR2211 #5 | UM449 | sup. | 5 ug | 1/1 | 20 ul |

This Example further demonstrates that the inventive Borrelia antigen DNA plasmid compositions are additionally useful for in vitro expression of antigen(s) (which by themselves are useful, e.g., for preparing antigenic, immunological or vaccine compositions or for diagnostic, detection, or assay purposes).

Example 4

Animal Study With VR2210

Two groups of five mice were injected with VR2210 (i.e., ten mice; mice A1–A5, B1–B5), and two groups of five mice (i.e., ten mice) were injected with plasmid VR1020 negative conrol DNA. VR1020 does not contain a coding sequence for a Borrelia antigen. The plasmid and control DNA were diluted in standard saline. Three bilateral injections of DNA were given at two week intervals at a dosage of 50 μg/leg into the rectus femoris muscle. Sera were collected 12 days after each injection and analyzed by 1) Antibody ELISA and 2) Growth Inhibition of Spirochetes. Titers after the first and third injections (Titer #1, Titer #3) are set forth below.

Two weeks after the last injection, mice were challenged with $10^4$ Sh2 spirochetes (same OspA serogroup as B31) injected intradermally in the tail. Sh2 is a virulent isolate of the same serogroup as B31. Mice were sacrificed 11 days following the challenge. Bladder, heart, plasma, and cross-cuttings of the tibiotarsal joints were cultured for 15 days at 34° C. in growth medium. Cultures were examined for the presence of spirochetes by phase-contrast microscopy and scored as negative if no spirochetes were seen in 50 high-power fields.

The antibody ELISA titers for the ten mice administered VR2210 are shown in the following Table. The titers were low after one injection and the group showed considerable variability in their immune response. After the third injection, however, the humoral immune response was uniformly high in 8 out of 10 mice with titers of greater than 1:40,000.

ANTIBODY ELISA TITERS
High passage B31 was the antigen used in the ELISA's.

| Mouse | Immunogen | Titer #1 | Titer #3 |
|---|---|---|---|
| A1 | ospA | 640 | 10240 |
| A2 | ospA | 640 | 10240 |
| A3 | ospA | 40 | >40,960 |
| A4 | ospA | 1280 | >40,960 |
| A5 | ospA | 1280 | >40,960 |
| B1 | ospA | <20 | >40,960 |
| B2 | ospA | <20 | >40,960 |
| B3 | ospA | 2560 | >40,960 |
| B4 | ospA | 5120–10,240 | >40,960 |
| B5 | ospA | 1280 | >40,960 |

No antibody binding to B31 (or immune response to B31) was observed for the mice administered the negative control DNA.

The following Table shows the Spirochete Growth Inhibition titers. The numbers indicate the maximal dilution of serum which inhibits spirochete growth in vitro. After the first injection of VR2210, growth inhibition was seen at serum dilutions of 32 to 128. After the third injection, however, inhibition of growth was detected at higher dilutions (up to 512), which is consistent with the antibody titer data.

Growth Inhibitory Titers

Method: Strain B31 spirochetes were mixed with an 8-fold dilution of serum and two-fold serially diluted in a 96-well plate. Guinea pig complement was added to each well to lyse the spirochetes which have bound antibody. The plates were covered with plastic seals and incubated for 72 hours at 34° C. Growth in each well was determined by observation of the phenol red indicator in the medium from red to yellow as well as by phase-contrast microscopy. The numbers were the maximal dilution of serum which inhibits spirochete growth in the well.

| Mouse | Immunogen | Titer #1 | Titer #3 |
|---|---|---|---|
| A1 | ospA | not determined | 256–512 |
| A2 | ospA | not determined | 128–256 |
| A3 | ospA | not determined | 256 |
| A4 | ospA | not determined | 64 |
| A5 | ospA | not determined | 64 |
| B1 | ospA | 32 | not determined |
| B2 | ospA | 64–128 | " |
| B3 | ospA | 64 | " |
| B4 | ospA | 64–128 | " |
| B5 | ospA | 64 | " |

No inhibition was observed with the sera of the mice administered the negative control DNA. The organ culture data shown in the following Table indicates that all ten VR2210 vaccinated mice were completely free of spirochetes in all tissues examined whereas all ten negative control mice had spirochetes in their bladder and joints. Therefore, vaccination with three doses of VR2210 gives 100% protection against spirochete challenge in vivo.

PRESENCE OF SPIROCHETES IN CULTURED ORGANS
Combined culture data for all groups. # Positive cultures/Total

| Immunogen | Plasma | Heart | Bladder | Joint |
|---|---|---|---|---|
| ospA | 0/10 | 0/10 | 0/10 | 0/10 |
| control | 3/10 | 7/10 | 10/10 | 10/10 |

This is a demonstration that the Borrelia DNA plasmid is effective against bacterial pathogenic targets. Immunization with VR2210 encoding OspA protects mice completely against intradermal challenge with 104 virulent spirochetes. This in vivo protection correlates with the serum IgG response measured both by antibody ELISA and by an in vitro spirochete growth inhibition assay.

The ability of the inventive composition to elicit a protective response capable of inhibiting spirochete growth demonstrates that the critical immunogenic epitopes on the bacterial protein are conserved when genes encoding these proteins are expressed in mammalian cells. This is particularly interesting and surprising because native OspA contains a lipid moiety on its N-terminus which has been shown to be a crucial determinant for the immunogenicity of the recombinant protein vaccine made from *E. coli*. In contrast, in the DNA and expression product of the invention, the natural OspA leader sequence which contains the lipidation signal has been replaced by the human TPA leader sequence in VR2210. Since this lipidation event is part of a post-translational processing step found uniquely in prokaryotic cells, it is unlikely that the lipid moiety is present on the VR2210 protein product. And thus, the results obtained by the present invention are indeed surprising and unexpected.

This Example also demonstrates that plasmids encoding OspB, such as VR2211, or another Borrelia antigen, e.g., OspC, or encoding multiple Borrelia antigens, e.g., OspA and OspB and/or OspC, is within the scope of the invention, and are useful. For instance, this Example demonstrates that the inventive *Borrelia burgdorferi* antigen DNA composition of the invention is useful for eliciting antibodies which have in vivo and in vitro uses (e.g., protective response; diagnostic, detection or assay purposes).

Example 5

Nucleic Acid Immunization

Immunization of mice

6–10 week old female C3H/HeN mice (Harlan Laboratories, IN) were immunized with plasmid VR2210 or VR1020 (control) diluted in sterile standard saline using a collared 28 G ½" (12.7 mm) nedle. 50 μg of plasmid was administered intra-muscularly into the rectus femoris muscle of each leg in a volume of 0.05 ml composition. Mice were boosted with identical composition on day 14 and day 28.

Challenge with infectious *Borrelia burgdorferi*

13 days following the second boost, mice were challenged with *Borrelia burgdorferi* Sh-2-82 (Erdile et al., 1993). $10^4$ *B. burgdorferi* Sh-2-82 in 10% v/v BSKII in PBS (pH 7.4) were injected intra-dermally at the base of the tail. This inoculum is 100 times the $ID_{50}$ for this strain of *B. burdorferi* (Erdile et al., 1993). Mice were sacrificed 10 days following challenge. Bladder, heart and cross-cuttings of tibiotarsal joints were aseptically removed and were placed in 6 ml BSKII containing antibiotics. Cultures were incubated at 34° C. After 15 days, organ cultures were examined by phase contrast microscopy for the presence of spirochaetes. Cultures were considered negative if no spirochaetes were seen in 20 high power fields.

ELISA

Wet, whole cell ELISAs were carried out as previously described (Sadziene et al., 1991) using high passage *B. burgdorferi* B31, strain B311 (Sadziene et al., 1995) as the antigen. Serial dilutions of mouse sera were made in 1% w/v dried non-fat milk in PBS (pH 7.4). Secondary antibody was goat anti-mouse IgG+IgM+IgA (H+L) conjugated to alkaline phosphatase (Zymed Laboratories, CA) used at a dilution of 1:1000 in PBS/1% milk. Plates were developed as previously described (Sadziene et al., 1991). Absorbance was read at 490 nm on a Dynatech 580 plate reader. Samples were considered positive if the absorbance value was greater than the mean +3 standard deviations of the mean of that for non-immune and control sera (Burkot et al., 1994).

In vitro growth inhibition assays

Growth inhibitory titers (GI titers) of the sera from the immunized mice were determined as previously described by Sadziene et al., 1993). Two (2) hemolytic units of unheated guinea pig complement (Calbiochem, CA) was added to each of the wells of the microtiter plate to give a final concentration of $10HU.ml^{-1}$ of medium after the addition of antibody. Wells were monitored visually for changes in the color of the phenol red indicator in the medium and by phase contrast microscopy of set mounts of well contents. The GI titer was defined as the lowest dilution of antiserum that resulted in pink instead of yellow wells and represented at least 20-fold fewer cells than in wells with no serum added.

PAGE and immunoblotting

PAGE and immunoblot were carried out as described previously (Sadziene et al., 1995). Twenty four micrograms of recombinant lipidated OspA (see Erdile et al., 1993, U.S. Ser. No. 08/373,455) or *B. burgdorferi* B31 were run on preparative polyacrylamide gels and were then transferred onto nitrocellulose membranes. Immunoblots were dried and stored at 4° C. until needed.

Immunization of mice with VR2210 resulted in an OspA-specific antibody response

Figure 19:
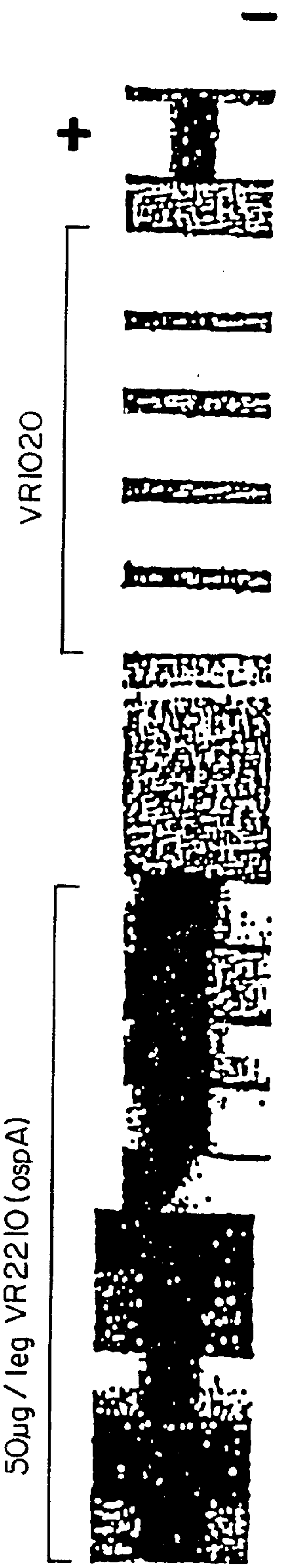
FIG. 19 shows an immunoblot.

Immunoblot of sera from the mice showed that those that received the plasmid bearing the *B. burgdorferi* B31 ospA gene, VR2210, developed an OspA-specific antibody response (FIG. 19). ELISA of the sera also showed that these mice had mounted a significant antibody response against B31. The geometric mean reciprocal ELISA titers are given in the following Table. The sera from the mice that received the plasmid with no Borrelia gene inserted, VR 1020, did not demonstrate an antibody response to *B. burgdorferi*. The sera from the VR2210-immunized mice were also found to inhibit growth of *B. burgdorferi* in vitro, to the same level as sera known to be protective. The geometric mean reciprocal GI titers of the sera are also given in the following Table.

The Table also shows the reciprocal geometric mean ELISA titers of the sera from the VR2210-immunized mice when IP- 90 (*B. garinii*) and ACA-I (*B. afzelli*) were used as antigen (sera are from the bleed taken 2 days before challenge).

Challenge with infectious *B. burgdorferi*

The results of the challenge of the DNA-immunized mice with *B. burgdorferi* Sh-2-82 are shown in the following Table. All mice which received VR2210 were protected against challenge, whereas Borrelias were recovered from all the mice that received the VR1020 plasmid.

Table

Reciprocal geometric mean ELISA titers and GI titers and results of infectious challenge of mice immunized with DNA constructs VR2210 and VR1020.

| | ELISA TITER | | | GI | CULTURE |
|---|---|---|---|---|---|
| Immunogen | B31 | IP-90 | ACA-I | TITER | POSITIVE* |
| VR2210 (ospA) | 54,696 | 2941 | 2389 | 388 | 0/10 |
| VR1020 (no insert) | ≦20 | ≦20 | ≦20 | ≦8 | 10/10 |

*Culture positive at one or more sites.

The results in this Table show that the invention is applicable to genospecies *burgdorferi, garinii* and *afzelli*; and need not be limited to *burgdorferi* or B31.

FIG. 19 is an immunoblot of *Borrelia burgdorferi* rOspA probed with sera from mice immunized with either plasmid VR2210 (ospA) or VR1020. Sera were diluted 1:100. The positive control (+) was H5332 (anti-OspA) monoclonal hybridoma supernatant, diluted 1:10.

The immunization was repeated with the plasmid construct VR2211, containing the ospB of *Borrelia burgdorferi* B31. An additional boost of this plasmid was given two weeks after the second boost. The 5 mice that received this construct, along with three mice that received VR1020, were challenged, and are sacrificed later. OspB-specific antibodies in sera from the VR2211 (ospB) immunized mice were detected on Western blots.

Also, the VR2210 immunization was repeated, along with rOspA lipoprotein controls (immunized subcutaneously or intra-muscularly with 1 μg) (5 mice per group) and the mice are bled every 2 weeks to assess the duration of the immune response to OspA by ELISA and growth inhibition assay. The results parallel those provided above.

This Example demonstrates that Borrelia antigen DNA compositions of the invention are useful for eliciting an in vivo response, which response can be protective against infection (and ergo against Lyme Disease); and, that the compositions of the invention are useful for merely eliciting antibodies, which by themselves are useful (e.g., for diagnostic, detection or assay purposes).

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Barbour, A. G. and Fish, D. The biological and social phenomenon of Lyme Disease. *Science.* 1993, 260, 1610–1616.
2. Fikrig, E., Barthold, S. W., Kantor, F. S. and Flavell, R. A. Protection of mice against the Lyme disease agent by immunizing with recombinant OspA. *Science.* 1990, 250, 553–556.
3. Erdile, L. f., Brandt, M., Warakomski, D. J., Westrack, G. J., Sadziene, A., Barbour, A. G. and Mays, J. P. Role of attached lipid in immunogenicity of *Borrelia burgdorferi* OspA. *Infect. Immun.* 1993, 61, 81–90. See also U.S. Ser. No. 08/373,455.
4. Keller, D., Kister, F. T., Marks, D. H., Hosback, P., Erdile, L. F. and Mays, J. P. Safety and immunogenicity of a recombinant outer surface protein A Lyme vaccine. *J. Am. Med. Assoc.* 1994, 271, 1764.
5. Sadziene, A., Thomas, D. D., Bundoc, V. G., Holt, S. H., and Barbour, A. G. A flagella-less mutant of *Borrelia burgdorferi*. J. Clin. Invest. 1991, 88, 82–92.
6. Sadziene, A., Thomas, D. D., and Barbour, A. G. *Borrelia burgdorferi* mutant lacing Osp: biological and immunological characterization. *Infect. Immun.* 1995, 63, 1573–1580.
7. Burkot, T. R., Piesman, J., and Wirtz, R. A. Quantitation of the *Borrelia burgdorferi* outer surface protein A in Ixodes scapularis: fluctuations during the tick life cycle, doubling times, and loss while feeding. *J. Infect. Dis.* 1994, 170, 883–889.
8. Sadziene, A., Thompson, P. A., and Barbour, A. G. In vitro inhibition of *Borrelia burgdorferi* growth by antibodies. J. Infect. Dis. 1993, 167, 165–172.
9. Bergstrom, S., Bundoc V. G., and Barbour, A. G. (1989). Molecular analysis of linear plasmid-encoded major surface proteins OspA and OspB, of the Lyme disease spirochaete *Borrelia burgdorferi*. Mol. Microbiol. 3:479–486.

What is claimed is:

1. A plasmid for expression of a Borrelia protein antigen wherein the Borrelia is selected from the group consisting of *Borrelia burgdorferi, Borrelia garinii* and *Borrelia afzelli* and the protein antigen is selected from the group consisting of OspA and OspB, said plasmid comprising DNA encoding the Borrelia protein antigen operatively linked to regulatory sequences which control expression and secretion of the Borrelia protein antigen from a mammalian cell.

2. The plasmid of claim 1 comprising from upstream to downstream: DNA encoding a promoter for driving expression in a eukaryotic cell, DNA encoding a eukaryotic leader peptide for facilitating secretion of a prokaryotic protein sequence from a mammalian cell, DNA encoding the Borrelia protein antigen, and DNA encoding a terminator.

3. The plasmid of claim 2 wherein the promoter is a mammalian virus promoter.

4. The plasmid of claim 3 wherein the promoter is a herpes virus promoter.

5. The plasmid of claim 4 wherein the promoter is a human cytomegalovirus promoter.

6. The plasmid of claim 5 wherein the DNA encoding a leader peptide is from DNA encoding human tissue plasminogen activator.

7. The plasmid of claim 6 wherein the DNA encoding a terminator is the 3' UTR transcriptional terminator from the gene encoding Bovine Growth Hormone.

8. The plasmid of claim 1 wherein the Borrelia protein antigen comprises an antigen from Borrelia burgdorferi.

9. The plasmid of claim 8, wherein the antigen is OspA thereof.

10. An immunological composition comprising a plasmid as claimed in claim 1 and a carrier or diluent.

11. An immunological composition comprising a plasmid as claimed in claim 8 and a carrier or diluent.

12. An immunological composition comprising a plasmid as claimed in claim 9 and a carrier or diluent.

13. A method for eliciting an immunological response in a host comprising intramuscularly administering to the host the composition as claim in claim 10, 11, or 12 wherein the Borrelia antigen is expressed, and wherein an immunological response in the host is elicited by the Borrelia antigen.

14. A method for expressing a Borrelia protein antigen in vitro comprising transfecting a eukaryotic cell with a plasmid as claimed in claim 1.

15. A method for expressing a Borrelia protein antigen in vitro comprising transfecting a eukaryotic cell with a plasmid as claimed in claim 1.

16. The method of claim 15 wherein the Borrelia protein antigen comprises OspA.

17.The method of claim 13 wherein the method is for eliciting a protective immunological response in the host against a *Borrelia burgdorferi* infection and the plasmid comprises DNA encoding an immunologically active OspA protein antigen of *Borrelia burgdorferi* which elicits a protective immunological response in the host.

18. The method of claim 17, wherein the *Borrelia burgdorferi* is *Borrelia burgdorferi* sensu stricto.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 5900 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
CTATATACTA CATCGTATCG TCATAGATAC GGTTACTCGT GTGTACTTAT AAGATGGCCA    60
TTGCATACGT TGTATCCATA TCATAATATG TACATTTATA TTGGCTCATG TCCAACATTA   120
CCGCCATGTT GACATTGATT ATTGACTAGT TATTAATAGT AATCAATTAC GGGGTCATTA   180
GTTCATAGCC CATATATGGA GTTCCGCGTT ACATAACTTA CGGTAAATGG CCCGCCTGGC   240
TGACCGCCCA ACGACCCCCG CCCATTGACG TCAATAATGA CGTATGTTCC CATAGTAACG   300
CCAATAGGGA CTTTCCATTG ACGTCAATGG GTGGAGTATT TACGGTAAAC TGCCCACTTG   360
GCAGTACATC AAGTGTATCA TATGCCAAGT ACGCCCCCTA TTGACGTCAA TGACGGTAAA   420
TGGCCCGCCT GGCATTATGC CCAGTACATG ACCTTATGGG ACTTTCCTAC TTGGCAGTAC   480
ATCTACGTAT TAGTCATCGC TATTACCATG GTGATGCGGT TTTGGCAGTA CATCAATGGG   540
CGTGGATAGC GGTTTGACTC ACGGGGATTT CCAAGTCTCC ACCCCATTGA CGTCAATGGG   600
AGTTTGTTTT GGCACCAAAA TCAACGGGAC TTTCCAAAAT GTCGTAACAA CTCCGCCCCA   660
TTGACGCAAA TGGGCGGTAG GCGTGTACGG TGGGAGGTCT ATATAAGCAG AGCTCGTTTA   720
```

-continued

GTGAACCGTC AGATCGCCTG GAGACGCCAT CCACGCTGTT TTGACCTCCA TAGAAGACAC 780

CGGGACCGAT CCAGCCTCCG CGGCCGGGAA CGGTGCATTG GAACGCGGAT TCCCCGTGCC 840

AAGAGTGACG TAAGTACCGC CTATAGAGTC TATAGGCCCA CCCCCTTGGC TTCTTATGCA 900

TGCTATACTG TTTTTGGCTT GGGGTCTATA CACCCCCGCT TCCTCATGTT ATAGGTGATG 960

GTATAGCTTA GCCTATAGGT GTGGGTTATT GACCATTATT GACCACTCCC CTATTGGTGA 1020

CGATACTTTC CATTACTAAT CCATAACATG GCTCTTTGCC ACAACTCTCT TTATTGGCTA 1080

TATGCCAATA CACTGTCCTT CAGAGACTGA CACGGACTCT GTATTTTTAC AGGATGGGGT 1140

CTCATTTATT ATTTACAAAT TCACATATAC AACACCACCG TCCCCAGTGC CCGCAGTTTT 1200

TATTAAACAT AACGTGGGAT CTCCACGCGA ATCTCGGGTA CGTGTTCCGG ACATGGGCTC 1260

TTCTCCGGTA GCGGCGGAGC TTCTACATCC GAGCCCTGCT CCCATGCCTC CAGCGACTCA 1320

TGGTCGCTCG GCAGCTCCTT GCTCCTAACA GTGGAGGCCA GACTTAGGCA CAGCACGATG 1380

CCCACCACCA CCAGTGTGCC GCACAAGGCC GTGGCGGTAG GGTATGTGTC TGAAAATGAG 1440

CTCGGGGAGC GGGCTTGCAC CGCTGACGCA TTTGGAAGAC TTAAGGCAGC GGCAGAAGAA 1500

GATGCAGGCA GCTGAGTTGT TGTGTTCTGA TAAGAGTCAG AGGTAACTCC CGTTGCGGTG 1560

CTGTTAACGG TGGAGGGCAG TGTAGTCTGA GCAGTACTCG TTGCTGCCGC GCGCGCCACC 1620

AGACATAATA GCTGACAGAC TAACAGACTG TTCCTTTCCA TGGGTCTTTT CTGCAGTCAC 1680

CGTCGTCGAC CAGAGCTGAG ATCCTACAGG AGTCCAGGGC TGGAGAGAAA ACCTCTGCGA 1740

GGAAAGGGAA GGAGCAAGCC GTGAATTTAA GGGACGCTGT GAAGCAATCA TGGATGCAAT 1800

GAAGAGAGGG CTCTGCTGTG TGCTGCTGCT GTGTGGAGCA GTCTTCGTTT CGCCCAGCGG 1860

TACCTGTAAG CAAAATGTTA GCAGCCTTGA CGAGAAAAAC AGCGTTTCAG TAGATTTGCC 1920

TGGTGAAATG AAAGTTCTTG TAAGCAAAGA AAAAAACAAA GACGGCAAGT ACGATCTAAT 1980

TGCAACAGTA GACAAGCTTG AGCTTAAAGG AACTTCTGAT AAAAACAATG GATCTGGAGT 2040

ACTTGAAGGC GTAAAAGCTG ACAAAAGTAA AGTAAAATTA ACAATTTCTG ACGATCTAGG 2100

TCAAACCACA CTTGAAGTTT TCAAAGAAGA TGGCAAAACA CTAGTATCAA AAAAAGTAAC 2160

TTCCAAAGAC AAGTCATCAA CAGAAGAAAA ATTCAATGAA AAAGGTGAAG TATCTGAAAA 2220

AATAATAACA AGAGCAGACG GAACCAGACT TGAATACACA GAAATTAAAA GCGATGGATC 2280

TGGAAAAGCT AAAGAGGTTT TAAAAGGCTA TGTTCTTGAA GGAACTCTAA CTGCTGAAAA 2340

AACAACATTG GTGGTTAAAG AAGGAACTGT TACTTTAAGC AAAAATATTT CAAAATCTGG 2400

GGAAGTTTCA GTTGAACTTA ATGACACTGA CAGTAGTGCT GCTACTAAAA AAACTGCAGC 2460

TTGGAATTCA GGCACTTCAA CTTTAACAAT TACTGTAAAC AGTAAAAAAA CTAAAGACCT 2520

TGTGTTTACA AAAGAAAACA CAATTACAGT ACAACAATAC GACTCAAATG GCACCAAATT 2580

AGAGGGGTCA GCAGTTGAAA TTACAAAACT TGATGAAATT AAAAACGCTC TTAAGTAAGG 2640

AGAATTTTCT AGACCAGGCG CCTGGATCCA GATCTGCTGT GCCTTCTAGT TGCCAGCCAT 2700

CTGTTGTTTG CCCCTCCCCC GTGCCTTCCT TGACCCTGGA AGGTGCCACT CCCACTGTCC 2760

TTTCCTAATA AAATGAGGAA ATTGCATCGC ATTGTCTGAG TAGGTGTCAT TCTATTCTGG 2820

GGGGTGGGGT GGGGCAGCAC AGCAAGGGGG AGGATTGGGA AGACAATAGC AGGCATGCTG 2880

GGGATGCGGT GGGCTCTATG GGTACCCAGG TGCTGAAGAA TTGACCCGGT TCCTCCTGGG 2940

CCAGAAAGAA GCAGGCACAT CCCCTTCTCT GTGACACACC CTGTCCACGC CCCTGGTTCT 3000

TAGTTCCAGC CCCACTCATA GGACACTCAT AGCTCAGGAG GGCTCCGCCT TCAATCCCAC 3060

CCGCTAAAGT ACTTGGAGCG GTCTCTCCCT CCCTCATCAG CCCACCAAAC CAAACCTAGC 3120

-continued

| | | | | | | |
|---|---|---|---|---|---|---|
| CTCCAAGAGT | GGGAAGAAAT | TAAAGCAAGA | TAGGCTATTA | AGTGCAGAGG | GAGAGAAAAT | 3180 |
| GCCTCCAACA | TGTGAGGAAG | TAATGAGAGA | AATCATAGAA | TTTCTTCCGC | TTCCTCGCTC | 3240 |
| ACTGACTCGC | TGCGCTCGGT | CGTTCGGCTG | CGGCGAGCGG | TATCAGCTCA | CTCAAAGGCG | 3300 |
| GTAATACGGT | TATCCACAGA | ATCAGGGGAT | AACGCAGGAA | AGAACATGTG | AGCAAAAGGC | 3360 |
| CAGCAAAAGG | CCAGGAACCG | TAAAAAGGCC | GCGTTGCTGG | CGTTTTTCCA | TAGGCTCCGC | 3420 |
| CCCCCTGACG | AGCATCACAA | AAATCGACGC | TCAAGTCAGA | GGTGGCGAAA | CCCGACAGGA | 3480 |
| CTATAAAGAT | ACCAGGCGTT | TCCCCCTGGA | AGCTCCCTCG | TGCGCTCTCC | TGTTCCGACC | 3540 |
| CTGCCGCTTA | CCGGATACCT | GTCCGCCTTT | CTCCCTTCGG | GAAGCGTGGC | GCTTTCTCAA | 3600 |
| TGCTCACGCT | GTAGGTATCT | CAGTTCGGTG | TAGGTCGTTC | GCTCCAAGCT | GGGCTGTGTG | 3660 |
| CACGAACCCC | CCGTTCAGCC | CGACCGCTGC | GCCTTATCCG | GTAACTATCG | TCTTGAGTCC | 3720 |
| AACCCGGTAA | GACACGACTT | ATCGCCACTG | GCAGCAGCCA | CTGGTAACAG | GATTAGCAGA | 3780 |
| GCGAGGTATG | TAGGCGGTGC | TACAGAGTTC | TTGAAGTGGT | GGCCTAACTA | CGGCTACACT | 3840 |
| AGAAGGACAG | TATTTGGTAT | CTGCGCTCTG | CTGAAGCCAG | TTACCTTCGG | AAAAAGAGTT | 3900 |
| GGTAGCTCTT | GATCCGGCAA | ACAAACCACC | GCTGGTAGCG | GTGGTTTTTT | TGTTTGCAAG | 3960 |
| CAGCAGATTA | CGCGCAGAAA | AAAAGGATCT | CAAGAAGATC | CTTTGATCTT | TTCTACGGGG | 4020 |
| TCTGACGCTC | AGTGGAACGA | AAACTCACGT | TAAGGGATTT | TGGTCATGAG | ATTATCAAAA | 4080 |
| AGGATCTTCA | CCTAGATCCT | TTTAAATTAA | AAATGAAGTT | TTAAATCAAT | CTAAAGTATA | 4140 |
| TATGAGTAAA | CTTGGTCTGA | CAGTTACCAA | TGCTTAATCA | GTGAGGCACC | TATCTCAGCG | 4200 |
| ATCTGTCTAT | TTCGTTCATC | CATAGTTGCC | TGACTCCGGG | GGGGGGGGGC | GCTGAGGTCT | 4260 |
| GCCTCGTGAA | GAAGGTGTTG | CTGACTCATA | CCAGGCCTGA | ATCGCCCCAT | CATCCAGCCA | 4320 |
| GAAAGTGAGG | GAGCCACGGT | TGATGAGAGC | TTTGTTGTAG | GTGGACCAGT | TGGTGATTTT | 4380 |
| GAACTTTTGC | TTTGCCACGG | AACGGTCTGC | GTTGTCGGGA | AGATGCGTGA | TCTGATCCTT | 4440 |
| CAACTCAGCA | AAAGTTCGAT | TTATTCAACA | AAGCCGCCGT | CCCGTCAAGT | CAGCGTAATG | 4500 |
| CTCTGCCAGT | GTTACAACCA | ATTAACCAAT | TCTGATTAGA | AAAACTCATC | GAGCATCAAA | 4560 |
| TGAAACTGCA | ATTTATTCAT | ATCAGGATTA | TCAATACCAT | ATTTTTGAAA | AAGCCGTTTC | 4620 |
| TGTAATGAAG | GAGAAAACTC | ACCGAGGCAG | TTCCATAGGA | TGGCAAGATC | CTGGTATCGG | 4680 |
| TCTGCGATTC | CGACTCGTCC | AACATCAATA | CAACCTATTA | ATTTCCCCTC | GTCAAAAATA | 4740 |
| AGGTTATCAA | GTGAGAAATC | ACCATGAGTG | ACGACTGAAT | CCGGTGAGAA | TGGCAAAAGC | 4800 |
| TTATGCATTT | CTTTCCAGAC | TTGTTCAACA | GGCCAGCCAT | TACGCTCGTC | ATCAAAATCA | 4860 |
| CTCGCATCAA | CCAAACCGTT | ATTCATTCGT | GATTGCGCCT | GAGCGAGACG | AAATACGCGA | 4920 |
| TCGCTGTTAA | AAGGACAATT | ACAAACAGGA | ATCGAATGCA | ACCGGCGCAG | GAACACTGCC | 4980 |
| AGCGCATCAA | CAATATTTTC | ACCTGAATCA | GGATATTCTT | CTAATACCTG | GAATGCTGTT | 5040 |
| TTCCCGGGGA | TCGCAGTGGT | GAGTAACCAT | GCATCATCAG | GAGTACGGAT | AAAATGCTTG | 5100 |
| ATGGTCGGAA | GAGGCATAAA | TTCCGTCAGC | CAGTTTAGTC | TGACCATCTC | ATCTGTAACA | 5160 |
| TCATTGGCAA | CGCTACCTTT | GCCATGTTTC | AGAAACAACT | CTGGCGCATC | GGGCTTCCCA | 5220 |
| TACAATCGAT | AGATTGTCGC | ACCTGATTGC | CCGACATTAT | CGCGAGCCCA | TTTATACCCA | 5280 |
| TATAAATCAG | CATCCATGTT | GGAATTTAAT | CGCGGCCTCG | AGCAAGACGT | TTCCCGTTGA | 5340 |
| ATATGGCTCA | TAACACCCCT | TGTATTACTG | TTTATGTAAG | CAGACAGTTT | TATTGTTCAT | 5400 |
| GATGATATAT | TTTTATCTTG | TGCAATGTAA | CATCAGAGAT | TTTGAGACAC | AACGTGGCTT | 5460 |
| TCCCCCCCCC | CCCATTATTG | AAGCATTTAT | CAGGGTTATT | GTCTCATGAG | CGGATACATA | 5520 |

-continued

| | | | | | | |
|---|---|---|---|---|---|---|
| TTTGAATGTA | TTTAGAAAAA | TAAACAAATA | GGGGTTCCGC | GCACATTTCC | CCGAAAAGTG | 5580 |
| CCACCTGACG | TCTAAGAAAC | CATTATTATC | ATGACATTAA | CCTATAAAAA | TAGGCGTATC | 5640 |
| ACGAGGCCCT | TTCGTCTCGC | GCGTTTCGGT | GATGACGGTG | AAAACCTCTG | ACACATGCAG | 5700 |
| CTCCCGGAGA | CGGTCACAGC | TTGTCTGTAA | GCGGATGCCG | GGAGCAGACA | AGCCCGTCAG | 5760 |
| GGCGCGTCAG | CGGGTGTTGG | CGGGTGTCGG | GGCTGGCTTA | ACTATGCGGC | ATCAGAGCAG | 5820 |
| ATTGTACTGA | GAGTGCACCA | TATGCGGTGT | GAAATACCGC | ACAGATGCGT | AAGGAGAAAA | 5880 |
| TACCGCATCA | GATTGGCTAT | | | | | 5900 |

(2) INFORMATION FOR SEQ ID NO:2:

(i) SEQUENCE CHARACTERISTICS:
(A) LENGTH: 5952 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| CTATATACTA | CATCGTATCG | TCATAGATCG | GTTACTCGTG | TGTACTTATA | AGATGGCCAT | 60 |
| TGCATACGTT | GTATCCATAT | CATAATATGT | ACATTTATAT | TGGCTCATGT | CCAACATTAC | 120 |
| CGCCATGTTG | ACATTGATTA | TTGACTAGTT | ATTAATAGTA | ATCAATTACG | GGGTCATTAG | 180 |
| TTCATAGCCC | ATATATGGAG | TTCCGCGTTA | CATAACTTAC | GGTAAATGGC | CCGCCTGGCT | 240 |
| GACCGCCCAA | CGACCCCCGC | CCATTGACGT | CAATAATGAC | GTATGTTCCC | ATAGTAACGC | 300 |
| CAATAGGGAC | TTTCCATTGA | CGTCAATGGG | TGGAGTATTT | ACGGTAAACT | GCCCACTTGG | 360 |
| CAGTACATCA | AGTGTATCAT | ATGCCAAGTA | CGCCCCCTAT | TGACGTCAAT | GACGGTAAAT | 420 |
| GGCCCGCCTG | GCATTATGCC | CAGTACATGA | CCTTATGGGA | CTTTCCTACT | TGGCAGTACA | 480 |
| TCTACGTATT | AGTCATCGCT | ATTACCATGG | TGATGCGGTT | TTGGCAGTAC | ATCAATGGGC | 540 |
| GTGGATAGCG | GTTTGACTCA | CGGGGATTTC | CAAGTCTCCA | CCCCATTGAC | GTCAATGGGA | 600 |
| GTTTGTTTTG | GCACCAAAAT | CAACGGGACT | TTCCAAAATG | TCGTAACAAC | TCCGCCCCAT | 660 |
| TGACGCAAAT | GGGCGGTAGG | CGTGTACGGT | GGGAGGTCTA | TATAAGCAGA | GCTCGTTTAG | 720 |
| TGAACCGTCA | GATCGCCTGG | AGACGCCATC | CACGCTGTTT | TGACCTCCAT | AGAAGACACC | 780 |
| GGGACCGATC | CAGCCTCCGC | GGCCGGGAAC | GGTGCATTGG | AACGCGGATT | CCCCGTGCCA | 840 |
| AGAGTGACGT | AAGTACCGCC | TATAGAGTCT | ATAGGCCCAC | CCCCTTGGCT | TCTTATGCAT | 900 |
| GCTATACTGT | TTTTGGCTTG | GGGTCTATAC | ACCCCCGCTT | CCTCATGTTA | TAGGTGATGG | 960 |
| TATAGCTTAG | CCTATAGGTG | TGGGTTATTG | ACCATTATTG | ACCACTCCCC | TATTGGTGAC | 1020 |
| GATACTTTCC | ATTACTAATC | CATAACATGG | CTCTTTGCCA | CAACTCTCTT | TATTGGCTAT | 1080 |
| ATGCCAATAC | ACTGTCCTTC | AGAGACTGAC | ACGGACTCTG | TATTTTTACA | GGATGGGGTC | 1140 |
| TCATTTATTA | TTTACAAATT | CACATATACA | ACACCACCGT | CCCCAGTGCC | CGCAGTTTTT | 1200 |
| ATTAAACATA | ACGTGGGATC | TCCACGCGAA | TCTCGGGTAC | GTGTTCCGGA | CATGGGCTCT | 1260 |
| TCTCCGGTAG | CGGCGGAGCT | TCTACATCCG | AGCCCTGCTC | CCATGCCTCC | AGCGACTCAT | 1320 |
| GGTCGCTCGG | CAGCTCCTTG | CTCCTAACAG | TGGAGGCCAG | ACTTAGGCAC | AGCACGATGC | 1380 |
| CCACCACCAC | CAGTGTGCCG | CACAAGGCCG | TGGCGGTAGG | GTATGTGTCT | GAAAATGAGC | 1440 |
| TCGGGGAGCG | GGCTTGCACC | GCTGACGCAT | TTGGAAGACT | TAAGGCAGCG | GCAGAAGAAG | 1500 |
| ATGCAGGCAG | CTGAGTTGTT | GTGTTCTGAT | AAGAGTCAGA | GGTAACTCCC | GTTGCGGTGC | 1560 |
| TGTTAACGGT | GGAGGGCAGT | GTAGTCTGAG | CAGTACTCGT | TGCTGCCGCG | CGCGCCACCA | 1620 |

-continued

GACATAATAG CTGACAGACT AACAGACTGT TCCTTTCCAT GGGTCTTTTC TGCAGTCACC 1680
GTCGTCGACC AGAGCTGAGA TCCTACAGGA GTCCAGGGCT GGAGAGAAAA CCTCTGCGAG 1740
GAAAGGGAAG GAGCAAGCCG TGAATTTAAG GGACGCTGTG AAGCAATCAT GGATGCAATG 1800
AAGAGAGGGC TCTGCTGTGT GCTGCTGCTG TGTGGAGCAG TCTTCGTTTC GCCCAGCGGT 1860
ACCTGTGCAC AAAAAGGTGC TGAGTCAATT GGTTCTCAAA AAGAAAATGA TCTAAACCTT 1920
GAAGACTCTA GTAAAAAATC ACATCAAAAC GCTAAACAAG ACCTTCCTGC GGTGACAGAA 1980
GACTCAGTGT CTTTGTTTAA TGGTAATAAA ATTTTTGTAA GCAAAGAAAA AAATAGCTCC 2040
GGCAAATATG ATTTAAGAGC AACAATTGAT CAGGTTGAAC TTAAAGGAAC TTCCGATAAA 2100
AACAATGGTT CTGGAACCCT TGAAGGTTCA AAGCCTGACA AGAGTAAAGT AAAATTAACA 2160
GTTTCTGCTG ATTTAAACAC AGTAACCTTA GAAGCATTTG ATGCCAGCAA CCAAAAAATT 2220
TCAAGTAAAG TTACTAAAAA ACAGGGGTCA ATAACAGAGG AAACTCTCAA AGCTAATAAA 2280
TTAGACTCAA AGAAATTAAC AAGATCAAAC GGAACTACAC TTGAATACTC ACAAATAACA 2340
GATGCTGACA ATGCTACAAA AGCAGTAGAA ACTCTAAAAA ATAGCATTAA GCTTGAAGGA 2400
AGTCTTGTAG TCGGAAAAAC AACAGTGGAA ATTAAAGAAG GTACTGTTAC TCTAAAAAGA 2460
GAAATTGAAA AAGATGGAAA AGTAAAAGTC TTTTTGAATG ACACTGCAGG TTCTAACAAA 2520
AAAACAGGTA AATGGGAAGA CAGTACTAGC ACTTTAACAA TTAGTGCTGA CAGCAAAAAA 2580
ACTAAAGATT TGGTGTTCTT AACAGATGGT ACAATTACAG TACAACAATA CAACACAGCT 2640
GGAACCAGCC TAGAAGGATC AGCAAGTGAA ATTAAAAATC TTTCAGAGCT TAAAAACGCT 2700
TTAAAATAAT ATATAGGATC CAGATCTGCT GTGCCTTCTA GTTGCCAGCC ATCTGTTGTT 2760
TGCCCCTCCC CCGTGCCTTC CTTGACCCTG GAAGGTGCCA CTCCCACTGT CCTTTCCTAA 2820
TAAAATGAGG AAATTGCATC GCATTGTCTG AGTAGGTGTC ATTCTATTCT GGGGGGTGGG 2880
GTGGGGCAGC ACAGCAAGGG GGAGGATTGG GAAGACAATA GCAGGCATGC TGGGGATGCG 2940
GTGGGCTCTA TGGGTACCCA GGTGCTGAAG AATTGACCCG GTTCCTCCTG GGCCAGAAAG 3000
AAGCAGGCAC ATCCCCTTCT CTGTGACACA CCCTGTCCAC GCCCCTGGTT CTTAGTTCCA 3060
GCCCCACTCA TAGGACACTC ATAGCTCAGG AGGGCTCCGC CTTCAATCCC ACCCGCTAAA 3120
GTACTTGGAG CGGTCTCTCC CTCCCTCATC AGCCCACCAA ACCAAACCTA GCCTCCAAGA 3180
GTGGGAAGAA ATTAAAGCAA GATAGGCTAT TAAGTGCAGA GGGAGAGAAA ATGCCTCCAA 3240
CATGTGAGGA AGTAATGAGA GAAATCATAG AATTTCTTCC GCTTCCTCGC TCACTGACTC 3300
GCTGCGCTCG GTCGTTCGGC TGCGGCGAGC GGTATCAGCT CACTCAAAGG CGGTAATACG 3360
GTTATCCACA GAATCAGGGG ATAACGCAGG AAAGAACATG TGAGCAAAAG GCCAGCAAAA 3420
GGCCAGGAAC CGTAAAAAGG CCGCGTTGCT GGCGTTTTTC CATAGGCTCC GCCCCCCTGA 3480
CGAGCATCAC AAAAATCGAC GCTCAAGTCA GAGGTGGCGA AACCCGACAG GACTATAAAG 3540
ATACCAGGCG TTTCCCCCTG GAAGCTCCCT CGTGCGCTCT CCTGTTCCGA CCCTGCCGCT 3600
TACCGGATAC CTGTCCGCCT TTCTCCCTTC GGGAAGCGTG GCGCTTTCTC AATGCTCACG 3660
CTGTAGGTAT CTCAGTTCGG TGTAGGTCGT TCGCTCCAAG CTGGGCTGTG TGCACGAACC 3720
CCCCGTTCAG CCCGACCGCT GCGCCTTATC CGGTAACTAT CGTCTTGAGT CCAACCCGGT 3780
AAGACACGAC TTATCGCCAC TGGCAGCAGC CACTGGTAAC AGGATTAGCA GAGCGAGGTA 3840
TGTAGGCGGT GCTACAGAGT TCTTGAAGTG GTGGCCTAAC TACGGCTACA CTAGAAGGAC 3900
AGTATTTGGT ATCTGCGCTC TGCTGAAGCC AGTTACCTTC GGAAAAAGAG TTGGTAGCTC 3960
TTGATCCGGC AAACAAACCA CCGCTGGTAG CGGTGGTTTT TTTGTTTGCA AGCAGCAGAT 4020

-continued

```
TACGCGCAGA AAAAAAGGAT CTCAAGAAGA TCCTTTGATC TTTTCTACGG GGTCTGACGC 4080
TCAGTGGAAC GAAAACTCAC GTTAAGGGAT TTTGGTCATG AGATTATCAA AAAGGATCTT 4140
CACCTAGATC CTTTTAAATT AAAAATGAAG TTTTAAATCA ATCTAAAGTA TATATGAGTA 4200
AACTTGGTCT GACAGTTACC AATGCTTAAT CAGTGAGGCA CCTATCTCAG CGATCTGTCT 4260
ATTTCGTTCA TCCATAGTTG CCTGACTCCG GGGGGGGGGG GCGCTGAGGT CTGCCTCGTG 4320
AAGAAGGTGT TGCTGACTCA TACCAGGCCT GAATCGCCCC ATCATCCAGC CAGAAAGTGA 4380
GGGAGCCACG GTTGATGAGA GCTTTGTTGT AGGTGGACCA GTTGGTGATT TTGAACTTTT 4440
GCTTTGCCAC GGAACGGTCT GCGTTGTCGG GAAGATGCGT GATCTGATCC TTCAACTCAG 4500
CAAAAGTTCG ATTTATTCAA CAAAGCCGCC GTCCCGTCAA GTCAGCGTAA TGCTCTGCCA 4560
GTGTTACAAC CAATTAACCA ATTCTGATTA GAAAAACTCA TCGAGCATCA AATGAAACTG 4620
CAATTTATTC ATATCAGGAT TATCAATACC ATATTTTTGA AAAAGCCGTT TCTGTAATGA 4680
AGGAGAAAAC TCACCGAGGC AGTTCCATAG GATGGCAAGA TCCTGGTATC GGTCTGCGAT 4740
TCCGACTCGT CCAACATCAA TACAACCTAT TAATTTCCCC TCGTCAAAAA TAAGGTTATC 4800
AAGTGAGAAA TCACCATGAG TGACGACTGA ATCCGGTGAG AATGGCAAAA GCTTATGCAT 4860
TTCTTTCCAG ACTTGTTCAA CAGGCCAGCC ATTACGCTCG TCATCAAAAT CACTCGCATC 4920
AACCAAACCG TTATTCATTC GTGATTGCGC CTGAGCGAGA CGAAATACGC GATCGCTGTT 4980
AAAAGGACAA TTACAAACAG GAATCGAATG CAACCGGCGC AGGAACACTG CCAGCGCATC 5040
AACAATATTT TCACCTGAAT CAGGATATTC TTCTAATACC TGGAATGCTG TTTTCCCGGG 5100
GATCGCAGTG GTGAGTAACC ATGCATCATC AGGAGTACGG ATAAAATGCT TGATGGTCGG 5160
AAGAGGCATA AATTCCGTCA GCCAGTTTAG TCTGACCATC TCATCTGTAA CATCATTGGC 5220
AACGCTACCT TTGCCATGTT TCAGAAACAA CTCTGGCGCA TCGGGCTTCC CATACAATCG 5280
ATAGATTGTC GCACCTGATT GCCCGACATT ATCGCGAGCC CATTTATACC CATATAAATC 5340
AGCATCCATG TTGGAATTTA ATCGCGGCCT CGAGCAAGAC GTTTCCCGTT GAATATGGCT 5400
CATAACACCC CTTGTATTAC TGTTTATGTA AGCAGACAGT TTTATTGTTC ATGATGATAT 5460
ATTTTTATCT TGTGCAATGT AACATCAGAG ATTTTGAGAC ACAACGTGGC TTTCCCCCCC 5520
CCCCCATTAT TGAAGCATTT ATCAGGGTTA TTGTCTCATG AGCGGATACA TATTTGAATG 5580
TATTTAGAAA AATAAACAAA TAGGGGTTCC GCGCACATTT CCCCGAAAAG TGCCACCTGA 5640
CGTCTAAGAA ACCATTATTA TCATGACATT AACCTATAAA AATAGGCGTA TCACGAGGCC 5700
CTTTCGTCTC GCGCGTTTCG GTGATGACGG TGAAAACCTC TGACACATGC AGCTCCCGGA 5760
GACGGTCACA GCTTGTCTGT AAGCGGATGC CGGGAGCAGA CAAGCCCGTC AGGGCGCGTC 5820
AGCGGGTGTT GGCGGGTGTC GGGGCTGGCT TAACTATGCG GCATCAGAGC AGATTGTACT 5880
GAGAGTGCAC CATATGCGGT GTGAAATACC GCACAGATGC GTAAGGAGAA AATACCGCAT 5940
CAGATTGGCT AT 5952
```

( 2 ) INFORMATION FOR SEQ ID NO:3:

( i ) SEQUENCE CHARACTERISTICS:
( A ) LENGTH: 5676 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

-continued

CTATATACTA CATCGTATCG TCATAGATCC GGTTACGTGT ACTTATAAGA TGGCCATTGC 60

ATACGTTGTA TCCATATCAT AATATGTACA TTTATATTGG CTCATGTCCA ACATTACCGC 120

CATGTTGACA TTGATTATTG ACTAGTTATT AATAGTAATC AATTACGGGG TCATTAGTTC 180

ATAGCCCATA TATGGAGTTC CGCGTTACAT AACTTACGGT AAATGGCCCG CCTGGCTGAC 240

CGCCCAACGA CCCCCGCCCA TTGACGTCAA TAATGACGTA TGTTCCCATA GTAACGCCAA 300

TAGGGACTTT CCATTGACGT CAATGGGTGG AGTATTTACG GTAAACTGCC CACTTGGCAG 360

TACATCAAGT GTATCATATG CCAAGTACGC CCCCTATTGA CGTCAATGAC GGTAAATGGC 420

CCGCCTGGCA TTATGCCCAG TACATGACCT TATGGGACTT TCCTACTTGG CAGTACATCT 480

ACGTATTAGT CATCGCTATT ACCATGGTGA TGCGGTTTTG GCAGTACATC AATGGGCGTG 540

GATAGCGGTT TGACTCACGG GGATTTCCAA GTCTCCACCC CATTGACGTC AATGGGAGTT 600

TGTTTTGGCA CCAAAATCAA CGGGACTTTC CAAAATGTCG TAACAACTCC GCCCCATTGA 660

CGCAAATGGG CGGTAGGCGT GTACGGTGGG AGGTCTATAT AAGCAGAGCT CGTTTAGTGA 720

ACCGTCAGAT CGCCTGGAGA CGCCATCCAC GCTGTTTTGA CCTCCATAGA AGACACCGGG 780

ACCGATCCAG CCTCCGCGGC CGGGAACGGT GCATTGGAAC GCGGATTCCC CGTGCCAAGA 840

GTGACGTAAG TACCGCCTAT AGAGTCTATA GGCCCACCCC CTTGGCTTCT TATGCATGCT 900

ATACTGTTTT TGGCTTGGGG TCTATACACC CCCGCTTCCT CATGTTATAG GTGATGGTAT 960

AGCTTAGCCT ATAGGTGTGG GTTATTGACC ATTATTGACC ACTCCCCTAT TGGTGACGAT 1020

ACTTTCCATT ACTAATCCAT AACATGGCTC TTTGCCACAA CTCTCTTTAT TGGCTATATG 1080

CCAATACACT GTCCTTCAGA GACTGACACG GACTCTGTAT TTTTACAGGA TGGGGTCTCA 1140

TTTATTATTT ACAAATTCAC ATATACAACA CCACCGTCCC CAGTGCCCGC AGTTTTTATT 1200

AAACATAACG TGGGATCTCC ACGCGAATCT CGGGTACGTG TTCCGGACAT GGGCTCTTCT 1260

CCGGTAGCGG CGGAGCTTCT ACATCCGAGC CCTGCTCCCA TGCCTCCAGC GACTCATGGT 1320

CGCTCGGCAG CTCCTTGCTC CTAACAGTGG AGGCCAGACT TAGGCACAGC ACGATGCCCA 1380

CCACCACCAG TGTGCCGCAC AAGGCCGTGG CGGTAGGGTA TGTGTCTGAA AATGAGCTCG 1440

GGGAGCGGGC TTGCACCGCT GACGCATTTG GAAGACTTAA GGCAGCGGCA GAAGAAGATG 1500

CAGGCAGCTG AGTTGTTGTG TTCTGATAAG AGTCAGAGGT AACTCCCGTT GCGGTGCTGT 1560

TAACGGTGGA GGGCAGTGTA GTCTGAGCAG TACTCGTTGC TGCCGCGCGC GCCACCAGAC 1620

ATAATAGCTG ACAGACTAAC AGACTGTTCC TTTCCATGGG TCTTTTCTGC AGTCACCGTC 1680

GTCGACCAGA GCTGAGATCC TACAGGAGTC CAGGGCTGGA GAGAAAACCT CTGCGAGGAA 1740

AGGGAAGGAG CAAGCCGTGA ATTTAAGGGA CGCTGTGAAG CAATCATGGA TGCAATGAAG 1800

AGAGGGCTCT GCTGTGTGCT GCTGCTGTGT GGAGCAGTCT TCGTTTCGCC CAGCGGTACC 1860

TGTAATAATT CAGGGAAAGA TGGGAATACA TCTGCAAATT CTGCTGATGA GTCTGTTAAA 1920

GGGCCTAATC TTACAGAAAT AAGTAAAAAA ATTACGGATT CTAATGCGGT TTTACTTGCT 1980

GTGAAAGAGG TTGAAGCGTT GCTGTCATCT ATAGATGAAA TTGCTGCTAA AGCTATTGGT 2040

AAAAAAATAC ACCAAAATAA TGGTTTGGAT ACCGAAAATA ATCACAATGG ATCATTGTTA 2100

GCGGGAGCTT ATGCAATATC AACCCTAATA AAACAAAAAT TAGATGGATT GAAAAATGAA 2160

GGATTAAAGG AAAAAATTGA TGCGGCTAAG AAATGTTCTG AAACATTTAC TAATAAATTA 2220

AAAGAAAAAC ACACAGATCT TGGTAAAGAA GGTGTTACTG ATGCTGATGC AAAAGAAGCG 2280

ATTTTAAAAA CAAATGGTAC TAAAACTAAA GGTGCTGAAG AACTTGGAAA ATTATTTGAA 2340

TCAGTAGAGG TCTTGTCAAA AGCAGCTAAA GAGATGCTTG CTAATTCAGT TAAAGAGCTT 2400

-continued

| | | | | | | |
|---|---|---|---|---|---|---|
| ACAAGCCCTG | TTGTGGCAGA | AAGTCCAAAA | AAACCTTAAG | GATCCAGATC | TGCTGTGCCT | 2460 |
| TCTAGTTGCC | AGCCATCTGT | TGTTTGCCCC | TCCCCCGTGC | CTTCCTTGAC | CCTGGAAGGT | 2520 |
| GCCACTCCCA | CTGTCCTTTC | CTAATAAAAT | GAGGAAATTG | CATCGCATTG | TCTGAGTAGG | 2580 |
| TGTCATTCTA | TTCTGGGGGG | TGGGGTGGGG | CAGCACAGCA | AGGGGGAGGA | TTGGGAAGAC | 2640 |
| AATAGCAGGC | ATGCTGGGGA | TGCGGTGGGC | TCTATGGGGA | CCCAGGTGCT | GAAGAATTGA | 2700 |
| CCCGGTTCCT | CCTGGGCCAG | AAAGAAGCAG | GCACATCCCC | TTCTCTGTGA | CACACCCTGT | 2760 |
| CCACGCCCCT | GGTTCTTAGT | TCCAGCCCCA | CTCATAGGAC | ACTCATAGCT | CAGGAGGGCT | 2820 |
| CCGCCTTCAA | TCCCACCCGC | TAAAGTACTT | GGAGCGGTCT | CTCCCTCCCT | CATCAGCCCA | 2880 |
| CCAAACCAAA | CCTAGCCTCC | AAGAGTGGGA | AGAAATTAAA | GCAAGATAGG | CTATTAAGTG | 2940 |
| CAGAGGGAGA | GAAAATGCCT | CCAACATGTG | AGGAAGTAAT | GAGAGAAATC | ATAGAATTTC | 3000 |
| TTCCGCTTCC | TCGCTCACTG | ACTCGCTGCG | CTCGGTCGTT | CGGCTGCGGC | GAGCGGTATC | 3060 |
| AGCTCACTCA | AAGGCGGTAA | TACGGTTATC | CACAGAATCA | GGGGATAACG | CAGGAAAGAA | 3120 |
| CATGTGAGCA | AAAGGCCAGC | AAAAGGCCAG | GAACCGTAAA | AAGGCCGCGT | TGCTGGCGTT | 3180 |
| TTTCCATAGG | CTCCGCCCCC | CTGACGAGCA | TCACAAAAAT | CGACGCTCAA | GTCAGAGGTG | 3240 |
| GCGAAACCCG | ACAGGACTAT | AAAGATACCA | GGCGTTTCCC | CCTGGAAGCT | CCCTCGTGCG | 3300 |
| CTCTCCTGTT | CCGACCCTGC | CGCTTACCGG | ATACCTGTCC | GCCTTTCTCC | CTTCGGGAAG | 3360 |
| CGTGGCGCTT | TCTCAATGCT | CACGCTGTAG | GTATCTCAGT | TCGGTGTAGG | TCGTTCGCTC | 3420 |
| CAAGCTGGGC | TGTGTGCACG | AACCCCCCGT | TCAGCCCGAC | CGCTGCGCCT | TATCCGGTAA | 3480 |
| CTATCGTCTT | GAGTCCAACC | CGGTAAGACA | CGACTTATCG | CCACTGGCAG | CAGCCACTGG | 3540 |
| TAACAGGATT | AGCAGAGCGA | GGTATGTAGG | CGGTGCTACA | GAGTTCTTGA | AGTGGTGGCC | 3600 |
| TAACTACGGC | TACACTAGAA | GGACAGTATT | TGGTATCTGC | GCTCTGCTGA | AGCCAGTTAC | 3660 |
| CTTCGGAAAA | AGAGTTGGTA | GCTCTTGATC | CGGCAAACAA | ACCACCGCTG | GTAGCGGTGG | 3720 |
| TTTTTTTGTT | TGCAAGCAGC | AGATTACGCG | CAGAAAAAAA | GGATCTCAAG | AAGATCCTTT | 3780 |
| GATCTTTTCT | ACGGGGTCTG | ACGCTCAGTG | GAACGAAAAC | TCACGTTAAG | GGATTTTGGT | 3840 |
| CATGAGATTA | TCAAAAAGGA | TCTTCACCTA | GATCCTTTTA | AATTAAAAAT | GAAGTTTTAA | 3900 |
| ATCAATCTAA | AGTATATATG | AGTAAACTTG | GTCTGACAGT | TACCAATGCT | TAATCAGTGA | 3960 |
| GGCACCTATC | TCAGCGATCT | GTCTATTTCG | TTCATCCATA | GTTGCCTGAC | TCCGGGGGGG | 4020 |
| GGGGGCGCTG | AGGTCTGCCT | CGTGAAGAAG | GTGTTGCTGA | CTCATACCAG | GCCTGAATCG | 4080 |
| CCCCATCATC | CAGCCAGAAA | GTGAGGGAGC | CACGGTTGAT | GAGAGCTTTG | TTGTAGGTGG | 4140 |
| ACCAGTTGGT | GATTTTGAAC | TTTTGCTTTG | CCACGGAACG | GTCTGCGTTG | TCGGGAAGAT | 4200 |
| GCGTGATCTG | ATCCTTCAAC | TCAGCAAAAG | TTCGATTTAT | TCAACAAAGC | CGCCGTCCCG | 4260 |
| TCAAGTCAGC | GTAATGCTCT | GCCAGTGTTA | CAACCAATTA | ACCAATTCTG | ATTAGAAAAA | 4320 |
| CTCATCGAGC | ATCAAATGAA | ACTGCAATTT | ATTCATATCA | GGATTATCAA | TACCATATTT | 4380 |
| TTGAAAAAGC | CGTTTCTGTA | ATGAAGGAGA | AAACTCACCG | AGGCAGTTCC | ATAGGATGGC | 4440 |
| AAGATCCTGG | TATCGGTCTG | CGATTCCGAC | TCGTCCAACA | TCAATACAAC | CTATTAATTT | 4500 |
| CCCCTCGTCA | AAAATAAGGT | TATCAAGTGA | GAAATCACCA | TGAGTGACGA | CTGAATCCGG | 4560 |
| TGAGAATGGC | AAAAGCTTAT | GCATTTCTTT | CCAGACTTGT | TCAACAGGCC | AGCCATTACG | 4620 |
| CTCGTCATCA | AAATCACTCG | CATCAACCAA | ACCGTTATTC | ATTCGTGATT | GCGCCTGAGC | 4680 |
| GAGACGAAAT | ACGCGATCGC | TGTTAAAAGG | ACAATTACAA | ACAGGAATCG | AATGCAACCG | 4740 |
| GCGCAGGAAC | ACTGCCAGCG | CATCAACAAT | ATTTTCACCT | GAATCAGGAT | ATTCTTCTAA | 4800 |

-continued

| | | | | | | |
|---|---|---|---|---|---|---|
| TACCTGGAAT | GCTGTTTTCC | CGGGGATCGC | AGTGGTGAGT | AACCATGCAT | CATCAGGAGT | 4860 |
| ACGGATAAAA | TGCTTGATGG | TCGGAAGAGG | CATAAATTCC | GTCAGCCAGT | TTAGTCTGAC | 4920 |
| CATCTCATCT | GTAACATCAT | TGGCAACGCT | ACCTTTGCCA | TGTTTCAGAA | ACAACTCTGG | 4980 |
| CGCATCGGGC | TTCCCATACA | ATCGATAGAT | TGTCGCACCT | GATTGCCCGA | CATTATCGCG | 5040 |
| AGCCCATTTA | TACCCATATA | AATCAGCATC | CATGTTGGAA | TTTAATCGCG | GCCTAGAGCA | 5100 |
| AGACGTTTCC | CGTTGAATAT | GGCTCATAAC | ACCCCTTGTA | TTACTGTTTA | TGTAAGCAGA | 5160 |
| CAGTTTTATT | GTTCATGATG | ATATATTTTT | ATCTTGTGCA | ATGTAACATC | AGAGATTTTG | 5220 |
| AGACACAACG | TGGCTTTCCC | CCCCCCCCCA | TTATTGAAGC | ATTTATCAGG | GTTATTGTCT | 5280 |
| CATGAGCGGA | TACATATTTG | AATGTATTTA | GAAAAATAAA | CAAATAGGGG | TTCCGCGCAC | 5340 |
| ATTTCCCCGA | AAAGTGCCAC | CTGACGTCTA | AGAAACCATT | ATTATCATGA | CATTAACCTA | 5400 |
| TAAAAATAGG | CGTATCACGA | GGCCCTTTCG | TCTCGCGCGT | TTCGGTGATG | ACGGTGAAAA | 5460 |
| CCTCTGACAC | ATGCAGCTCC | CGGAGACGGT | CACAGCTTGT | CTGTAAGCGG | ATGCCGGGAG | 5520 |
| CAGACAAGCC | CGTCAGGGCG | CGTCAGCGGG | TGTTGGCGGG | TGTCGGGGCT | GGCTTAACTA | 5580 |
| TGCGGCATCA | GAGCAGATTG | TACTGAGAGT | GCACCATATG | CGGTGTGAAA | TACCGCACAG | 5640 |
| ATGCGTAAGG | AGAAAATACC | GCATCAGATT | GGCTAT | | | 5676 |

( 2 ) INFORMATION FOR SEQ ID NO:4:

( i ) SEQUENCE CHARACTERISTICS:
( A ) LENGTH: 5682 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| CTATATACTA | CATCGTATCG | TCATAGATCC | GGTTACGTGT | ACTTATAAGA | TGGCCATTGC | 60 |
| ATACGTTGTA | TCCATATCAT | AATATGTACA | TTTATATTGG | CTCATGTCCA | ACATTACCGC | 120 |
| CATGTTGACA | TTGATTATTG | ACTAGTTATT | AATAGTAATC | AATTACGGGG | TCATTAGTTC | 180 |
| ATAGCCCATA | TATGGAGTTC | CGCGTTACAT | AACTTACGGT | AAATGGCCCG | CCTGGCTGAC | 240 |
| CGCCCAACGA | CCCCCGCCCA | TTGACGTCAA | TAATGACGTA | TGTTCCCATA | GTAACGCCAA | 300 |
| TAGGGACTTT | CCATTGACGT | CAATGGGTGG | AGTATTTACG | GTAAACTGCC | CACTTGGCAG | 360 |
| TACATCAAGT | GTATCATATG | CCAAGTACGC | CCCCTATTGA | CGTCAATGAC | GGTAAATGGC | 420 |
| CCGCCTGGCA | TTATGCCCAG | TACATGACCT | TATGGGACTT | TCCTACTTGG | CAGTACATCT | 480 |
| ACGTATTAGT | CATCGCTATT | ACCATGGTGA | TGCGGTTTTG | GCAGTACATC | AATGGGCGTG | 540 |
| GATAGCGGTT | TGACTCACGG | GGATTTCCAA | GTCTCCACCC | CATTGACGTC | AATGGGAGTT | 600 |
| TGTTTTGGCA | CCAAAATCAA | CGGGACTTTC | CAAAATGTCG | TAACAACTCC | GCCCCATTGA | 660 |
| CGCAAATGGG | CGGTAGGCGT | GTACGGTGGG | AGGTCTATAT | AAGCAGAGCT | CGTTTAGTGA | 720 |
| ACCGTCAGAT | CGCCTGGAGA | CGCCATCCAC | GCTGTTTTGA | CCTCCATAGA | AGACACCGGG | 780 |
| ACCGATCCAG | CCTCCGCGGC | CGGGAACGGT | GCATTGGAAC | GCGGATTCCC | CGTGCCAAGA | 840 |
| GTGACGTAAG | TACCGCCTAT | AGAGTCTATA | GGCCCACCCC | CTTGGCTTCT | TATGCATGCT | 900 |
| ATACTGTTTT | TGGCTTGGGG | TCTATACACC | CCCGCTTCCT | CATGTTATAG | GTGATGGTAT | 960 |
| AGCTTAGCCT | ATAGGTGTGG | GTTATTGACC | ATTATTGACC | ACTCCCCTAT | TGGTGACGAT | 1020 |
| ACTTTCCATT | ACTAATCCAT | AACATGGCTC | TTTGCCACAA | CTCTCTTTAT | TGGCTATATG | 1080 |
| CCAATACACT | GTCCTTCAGA | GACTGACACG | GACTCTGTAT | TTTTACAGGA | TGGGGTCTCA | 1140 |

-continued

```
TTTATTATTT ACAAATTCAC ATATACAACA CCACCGTCCC CAGTGCCCGC AGTTTTTATT   1200
AAACATAACG TGGGATCTCC ACGCGAATCT CGGGTACGTG TTCCGGACAT GGGCTCTTCT   1260
CCGGTAGCGG CGGAGCTTCT ACATCCGAGC CCTGCTCCCA TGCCTCCAGC GACTCATGGT   1320
CGCTCGGCAG CTCCTTGCTC CTAACAGTGG AGGCCAGACT TAGGCACAGC ACGATGCCCA   1380
CCACCACCAG TGTGCCGCAC AAGGCCGTGG CGGTAGGGTA TGTGTCTGAA AATGAGCTCG   1440
GGGAGCGGGC TTGCACCGCT GACGCATTTG GAAGACTTAA GGCAGCGGCA GAAGAAGATG   1500
CAGGCAGCTG AGTTGTTGTG TTCTGATAAG AGTCAGAGGT AACTCCCGTT GCGGTGCTGT   1560
TAACGGTGGA GGGCAGTGTA GTCTGAGCAG TACTCGTTGC TGCCGCGCGC GCCACCAGAC   1620
ATAATAGCTG ACAGACTAAC AGACTGTTCC TTTCCATGGG TCTTTTCTGC AGTCACCGTC   1680
GTCGACCAGA GCTGAGATCC TACAGGAGTC CAGGGCTGGA GAGAAAACCT CTGCGAGGAA   1740
AGGGAAGGAG CAAGCCGTGA ATTTAAGGGA CGCTGTGAAG CAATCATGGA TGCAATGAAG   1800
AGAGGGCTCT GCTGTGTGCT GCTGCTGTGT GGAGCAGTCT TCGTTTCGCC CAGCGGTACC   1860
TGTAATAATT CAGGGAAAGG TGGGGATTCT GCATCTACTA ATCCTGCTGA CGAGTCTGCG   1920
AAAGGGCCTA ATCTTACAGA AATAAGCAAA AAAATTACAG ATTCTAATGC ATTTGTACTT   1980
GCTGTTAAAG AAGTTGAGAC TTTGGTTTTA TCTATAGATG AACTTGCTAA GAAAGCTATA   2040
GGTCAAAAAA TAGACAATAA TAATGGTTTA GCTGCTTTAA ATAATCAGAA TGGATCGTTG   2100
TTAGCAGGAG CCTATGCAAT ATCAACCCTA ATAACAGAAA AATTGAGTAA ATTGAAAAAT   2160
TTAGAAGAAT TAAAGACAGA AATTGCAAAG GCTAAGAAAT GTTCCGAAGA ATTTACTAAT   2220
AAACTAAAAA GTGGTCATGC AGATCTTGGC AAACAGGATG CTACCGATGA TCATGCAAAA   2280
GCAGCTATTT TAAAAACACA TGCAACTACC GATAAAGGTG CTAAAGAATT TAAAGATTTA   2340
TTTGAATCAG TAGAAGGTTT GTTAAAAGCA GCTCAAGTAG CACTAACTAA TTCAGTTAAA   2400
GAACTTACAA GTCCTGTTGT AGCAGAAAGT CCAAAAAAAC CTTAAGGATC CAGATCTGCT   2460
GTGCCTTCTA GTTGCCAGCC ATCTGTTGTT TGCCCCTCCC CCGTGCCTTC CTTGACCCTG   2520
GAAGGTGCCA CTCCCACTGT CCTTTCCTAA TAAAATGAGG AAATTGCATC GCATTGTCTG   2580
AGTAGGTGTC ATTCTATTCT GGGGGGTGGG GTGGGGCAGC ACAGCAAGGG GGAGGATTGG   2640
GAAGACAATA GCAGGCATGC TGGGGATGCG GTGGGCTCTA TGGGGACCCA GGTGCTGAAG   2700
AATTGACCCG GTTCCTCCTG GGCCAGAAAG AAGCAGGCAC ATCCCCTTCT CTGTGACACA   2760
CCCTGTCCAC GCCCCTGGTT CTTAGTTCCA GCCCCACTCA TAGGACACTC ATAGCTCAGG   2820
AGGGCTCCGC CTTCAATCCC ACCCGCTAAA GTACTTGGAG CGGTCTCTCC CTCCCTCATC   2880
AGCCCACCAA ACCAAACCTA GCCTCCAAGA GTGGGAAGAA ATTAAAGCAA GATAGGCTAT   2940
TAAGTGCAGA GGGAGAGAAA ATGCCTCCAA CATGTGAGGA AGTAATGAGA GAAATCATAG   3000
AATTTCTTCC GCTTCCTCGC TCACTGACTC GCTGCGCTCG GTCGTTCGGC TGCGGCGAGC   3060
GGTATCAGCT CACTCAAAGG CGGTAATACG GTTATCCACA GAATCAGGGG ATAACGCAGG   3120
AAAGAACATG TGAGCAAAAG GCCAGCAAAA GGCCAGGAAC CGTAAAAAGG CCGCGTTGCT   3180
GGCGTTTTTC CATAGGCTCC GCCCCCCTGA CGAGCATCAC AAAAATCGAC GCTCAAGTCA   3240
GAGGTGGCGA AACCCGACAG GACTATAAAG ATACCAGGCG TTTCCCCCTG GAAGCTCCCT   3300
CGTGCGCTCT CCTGTTCCGA CCCTGCCGCT TACCGGATAC CTGTCCGCCT TTCTCCCTTC   3360
GGGAAGCGTG GCGCTTTCTC AATGCTCACG CTGTAGGTAT CTCAGTTCGG TGTAGGTCGT   3420
TCGCTCCAAG CTGGGCTGTG TGCACGAACC CCCCGTTCAG CCCGACCGCT GCGCCTTATC   3480
CGGTAACTAT CGTCTTGAGT CCAACCCGGT AAGACACGAC TTATCGCCAC TGGCAGCAGC   3540
```

-continued

| | | | | | | |
|---|---|---|---|---|---|---|
| CACTGGTAAC | AGGATTAGCA | GAGCGAGGTA | TGTAGGCGGT | GCTACAGAGT | TCTTGAAGTG | 3600 |
| GTGGCCTAAC | TACGGCTACA | CTAGAAGGAC | AGTATTTGGT | ATCTGCGCTC | TGCTGAAGCC | 3660 |
| AGTTACCTTC | GGAAAAAGAG | TTGGTAGCTC | TTGATCCGGC | AAACAAACCA | CCGCTGGTAG | 3720 |
| CGGTGGTTTT | TTTGTTTGCA | AGCAGCAGAT | TACGCGCAGA | AAAAAAGGAT | CTCAAGAAGA | 3780 |
| TCCTTTGATC | TTTTCTACGG | GGTCTGACGC | TCAGTGGAAC | GAAAACTCAC | GTTAAGGGAT | 3840 |
| TTTGGTCATG | AGATTATCAA | AAAGGATCTT | CACCTAGATC | CTTTTAAATT | AAAAATGAAG | 3900 |
| TTTTAAATCA | ATCTAAAGTA | TATATGAGTA | AACTTGGTCT | GACAGTTACC | AATGCTTAAT | 3960 |
| CAGTGAGGCA | CCTATCTCAG | CGATCTGTCT | ATTTCGTTCA | TCCATAGTTG | CCTGACTCCG | 4020 |
| GGGGGGGGGG | GCGCTGAGGT | CTGCCTCGTG | AAGAAGGTGT | TGCTGACTCA | TACCAGGCCT | 4080 |
| GAATCGCCCC | ATCATCCAGC | CAGAAAGTGA | GGGAGCCACG | GTTGATGAGA | GCTTTGTTGT | 4140 |
| AGGTGGACCA | GTTGGTGATT | TTGAACTTTT | GCTTTGCCAC | GGAACGGTCT | GCGTTGTCGG | 4200 |
| GAAGATGCGT | GATCTGATCC | TTCAACTCAG | CAAAAGTTCG | ATTTATTCAA | CAAAGCCGCC | 4260 |
| GTCCCGTCAA | GTCAGCGTAA | TGCTCTGCCA | GTGTTACAAC | CAATTAACCA | ATTCTGATTA | 4320 |
| GAAAAACTCA | TCGAGCATCA | AATGAAACTG | CAATTTATTC | ATATCAGGAT | TATCAATACC | 4380 |
| ATATTTTTGA | AAAAGCCGTT | TCTGTAATGA | AGGAGAAAAC | TCACCGAGGC | AGTTCCATAG | 4440 |
| GATGGCAAGA | TCCTGGTATC | GGTCTGCGAT | TCCGACTCGT | CCAACATCAA | TACAACCTAT | 4500 |
| TAATTTCCCC | TCGTCAAAAA | TAAGGTTATC | AAGTGAGAAA | TCACCATGAG | TGACGACTGA | 4560 |
| ATCCGGTGAG | AATGGCAAAA | GCTTATGCAT | TTCTTTCCAG | ACTTGTTCAA | CAGGCCAGCC | 4620 |
| ATTACGCTCG | TCATCAAAAT | CACTCGCATC | AACCAAACCG | TTATTCATTC | GTGATTGCGC | 4680 |
| CTGAGCGAGA | CGAAATACGC | GATCGCTGTT | AAAAGGACAA | TTACAAACAG | GAATCGAATG | 4740 |
| CAACCGGCGC | AGGAACACTG | CCAGCGCATC | AACAATATTT | TCACCTGAAT | CAGGATATTC | 4800 |
| TTCTAATACC | TGGAATGCTG | TTTTCCCGGG | GATCGCAGTG | GTGAGTAACC | ATGCATCATC | 4860 |
| AGGAGTACGG | ATAAAATGCT | TGATGGTCGG | AAGAGGCATA | AATTCCGTCA | GCCAGTTTAG | 4920 |
| TCTGACCATC | TCATCTGTAA | CATCATTGGC | AACGCTACCT | TTGCCATGTT | TCAGAAACAA | 4980 |
| CTCTGGCGCA | TCGGGCTTCC | CATACAATCG | ATAGATTGTC | GCACCTGATT | GCCCGACATT | 5040 |
| ATCGCGAGCC | CATTTATACC | CATATAAATC | AGCATCCATG | TTGGAATTTA | ATCGCGGCCT | 5100 |
| AGAGCAAGAC | GTTTCCCGTT | GAATATGGCT | CATAACACCC | CTTGTATTAC | TGTTTATGTA | 5160 |
| AGCAGACAGT | TTTATTGTTC | ATGATGATAT | ATTTTTATCT | TGTGCAATGT | AACATCAGAG | 5220 |
| ATTTTGAGAC | ACAACGTGGC | TTTCCCCCCC | CCCCCATTAT | TGAAGCATTT | ATCAGGGTTA | 5280 |
| TTGTCTCATG | AGCGGATACA | TATTTGAATG | TATTTAGAAA | AATAAACAAA | TAGGGGTTCC | 5340 |
| GCGCACATTT | CCCCGAAAAG | TGCCACCTGA | CGTCTAAGAA | ACCATTATTA | TCATGACATT | 5400 |
| AACCTATAAA | AATAGGCGTA | TCACGAGGCC | CTTTCGTCTC | GCGCGTTTCG | GTGATGACGG | 5460 |
| TGAAAACCTC | TGACACATGC | AGCTCCCGGA | GACGGTCACA | GCTTGTCTGT | AAGCGGATGC | 5520 |
| CGGGAGCAGA | CAAGCCCGTC | AGGGCGCGTC | AGCGGGTGTT | GGCGGGTGTC | GGGGCTGGCT | 5580 |
| TAACTATGCG | GCATCAGAGC | AGATTGTACT | GAGAGTGCAC | CATATGCGGT | GTGAAATACC | 5640 |
| GCACAGATGC | GTAAGGAGAA | AATACCGCAT | CAGATTGGCT | AT | | 5682 |